(12) United States Patent
Kumar et al.

(10) Patent No.: US 7,236,816 B2
(45) Date of Patent: *Jun. 26, 2007

(54) BIOPSY AND SAMPLING NEEDLE ANTENNAS FOR MAGNETIC RESONANCE IMAGING-GUIDED BIOPSIES

(75) Inventors: Ananda Kumar, Baltimore, MD (US); Ergin Atalar, Columbia, MD (US); Ogan Ocali, Sunnyvale, CA (US)

(73) Assignee: Johns Hopkins University, Baltimore, MD (US)

( * ) Notice: Subject to any disclaimer, the term of this patent is extended or adjusted under 35 U.S.C. 154(b) by 1051 days.

This patent is subject to a terminal disclaimer.

(21) Appl. No.: 10/131,601

(22) Filed: Apr. 24, 2002

(65) Prior Publication Data

US 2003/0028094 A1   Feb. 6, 2003

Related U.S. Application Data

(63) Continuation-in-part of application No. 09/360,144, filed on Jul. 26, 1999, now abandoned, which is a continuation-in-part of application No. 08/638,934, filed on Apr. 25, 1996, now Pat. No. 5,928,145.

(60) Provisional application No. 60/286,271, filed on Apr. 25, 2001.

(51) Int. Cl.
*A61B 5/055* (2006.01)
(52) U.S. Cl. ............... 600/411; 600/423; 600/562; 600/567
(58) Field of Classification Search ............ 600/410, 600/411, 423, 562, 564, 567; 324/307, 309, 324/318, 322

See application file for complete search history.

(56) References Cited

U.S. PATENT DOCUMENTS 3,342,175 A    9/1967   Bulloch ................ 128/2

(Continued)

FOREIGN PATENT DOCUMENTS

EP    0 466 424 A1    1/1992

(Continued)

OTHER PUBLICATIONS

International Search Report, PCT Application No. PCT/US 02/12867, mailed Aug. 21, 2002.

(Continued)

*Primary Examiner*—Ruth S. Smith
(74) *Attorney, Agent, or Firm*—Myers Bigel Sibley & Sajovec PA

(57) ABSTRACT

Herein is disclosed a magnetic resonance imaging antenna, including an inner conductor, an outer shield slideably displaceable with respect to the inner conductor, and an insulator electrically insulating the inner conductor from the outer shield. Herein is disclosed a biopsy needle antenna, including a magnetic resonance imaging antenna, having an outer shield, and an inner conductor electrically insulated from the outer shield by a dielectric; and a biopsy needle electrically connected to the inner conductor and electrically insulated from the outer shield by the dielectric. Herein is disclosed a method of obtaining a sample with magnetic resonance imaging guidance, including providing a sampling needle magnetic resonance imaging antenna, advancing the antenna to a structure from which the sample is to be taken, detecting magnetic resonance data by the antenna, and coupling the sample to the antenna.

33 Claims, 13 Drawing Sheets

U.S. PATENT DOCUMENTS

| | | | |
|---|---|---|---|
| 4,431,005 A | 2/1984 | McCormick | 128/656 |
| 4,445,501 A | 5/1984 | Bresler | 128/1.5 |
| 4,572,198 A | 2/1986 | Codrington | 128/653 |
| 4,643,186 A | 2/1987 | Rosen et al. | 128/303.1 |
| 4,672,972 A | 6/1987 | Berke | 128/653 |
| 4,766,381 A | 8/1988 | Conturo et al. | 324/309 |
| 4,776,341 A | 10/1988 | Bachus et al. | 128/653 |
| 4,791,372 A | 12/1988 | Kirk et al. | 324/318 |
| 4,793,356 A | 12/1988 | Misic et al. | 128/653 |
| 4,813,429 A | 3/1989 | Eshel et al. | 128/736 |
| 4,823,812 A | 4/1989 | Eshel et al. | 128/804 |
| 4,858,613 A | 8/1989 | Fry et al. | 128/660.03 |
| 4,897,604 A | 1/1990 | Carlson et al. | 324/318 |
| 4,922,204 A | 5/1990 | Duerr et al. | 324/322 |
| 4,932,411 A | 6/1990 | Fritschy et al. | 128/653 |
| 4,960,106 A | 10/1990 | Kubokawa et al. | 128/6 |
| 5,019,075 A | 5/1991 | Spears et al. | 606/7 |
| 5,035,231 A | 7/1991 | Kubokawa et al. | 128/6 |
| 5,050,607 A | 9/1991 | Bradley et al. | 128/653 A |
| 5,090,959 A | 2/1992 | Samson et al. | 604/96 |
| 5,095,911 A | 3/1992 | Pomeranz | 128/662.06 |
| 5,099,208 A | 3/1992 | Fitzpatrick et al. | 324/312 |
| 5,167,233 A | 12/1992 | Eberle et al. | 128/662.06 |
| 5,170,789 A | 12/1992 | Narayan et al. | 128/653.5 |
| 5,190,046 A | 3/1993 | Shturman | 128/662.06 |
| 5,211,165 A | 5/1993 | Dumoulin et al. | 128/653.1 |
| 5,211,166 A | 5/1993 | Sepponen | 128/653.5 |
| 5,217,010 A | 6/1993 | Tsitlik et al. | 128/419 PG |
| 5,260,658 A | 11/1993 | Greim et al. | 324/322 |
| 5,270,485 A | 12/1993 | Jacobsen | 174/15.1 |
| 5,271,400 A | 12/1993 | Dumoulin et al. | 128/653.2 |
| 5,293,872 A | 3/1994 | Alfano et al. | 128/664 |
| 5,294,886 A | 3/1994 | Duerr | 324/318 |
| 5,307,808 A | 5/1994 | Dumoulin et al. | 128/653.2 |
| 5,307,814 A | 5/1994 | Kressel et al. | 128/653.5 |
| 5,318,025 A | 6/1994 | Dumoulin et al. | 128/653.2 |
| 5,323,778 A | 6/1994 | Kandarpa et al. | 128/653.2 |
| 5,347,221 A | 9/1994 | Rubinson | 324/318 |
| 5,348,010 A | 9/1994 | Schnall et al. | 128/653.2 |
| 5,352,979 A | 10/1994 | Conturo | 324/307 |
| 5,355,087 A | 10/1994 | Claiborne et al. | 324/322 |
| 5,358,515 A | 10/1994 | Hürter et al. | 607/101 |
| 5,365,928 A | 11/1994 | Rhinehart et al. | 128/653.5 |
| 5,370,644 A | 12/1994 | Langberg | 606/33 |
| 5,372,138 A | 12/1994 | Crowley et al. | 128/662.06 |
| 5,375,596 A | 12/1994 | Twiss et al. | 128/653.1 |
| 5,400,787 A | 3/1995 | Marandos | 128/653.5 |
| 5,413,104 A | 5/1995 | Buijs et al. | 128/653.5 |
| 5,419,325 A | 5/1995 | Dumoulin et al. | 128/653.2 |
| 5,421,338 A | 6/1995 | Crowley et al. | 128/662.06 |
| 5,429,132 A | 7/1995 | Guy et al. | 128/653.1 |
| 5,435,302 A | 7/1995 | Lenkinski et al. | 600/422 |
| 5,437,277 A | 8/1995 | Dumoulin et al. | 128/653.1 |
| 5,439,000 A | 8/1995 | Gunderson et al. | 128/664 |
| 5,443,066 A | 8/1995 | Dumoulin et al. | 128/653.1 |
| 5,443,489 A | 8/1995 | Ben-Haim | 607/115 |
| 5,447,156 A | 9/1995 | Dumoulin et al. | 128/653.2 |
| 5,451,232 A | 9/1995 | Rhinehart et al. | 606/192 |
| 5,451,774 A | 9/1995 | Jacobsen | 250/227.24 |
| 5,462,055 A | 10/1995 | Casey et al. | 128/653.5 |
| 5,476,095 A | 12/1995 | Schnall et al. | 128/653.2 |
| 5,498,261 A | 3/1996 | Strul | 606/29 |
| 5,507,743 A | 4/1996 | Edwards et al. | 606/41 |
| 5,512,825 A | 4/1996 | Atalar et al. | 324/309 |
| 5,520,644 A | 5/1996 | Imran | 604/95 |
| 5,524,630 A | 6/1996 | Crowley | 128/662.06 |
| 5,540,679 A | 7/1996 | Fram et al. | 606/27 |
| 5,558,093 A | 9/1996 | Pomeranz | 128/660.03 |
| 5,578,008 A | 11/1996 | Hara | 604/96 |
| 5,588,432 A | 12/1996 | Crowley | 128/660.03 |
| 5,598,097 A | 1/1997 | Scholes et al. | 324/316 |
| 5,609,606 A | 3/1997 | O'Boyle | 606/194 |
| 5,611,807 A | 3/1997 | O'Boyle | 606/169 |
| 5,617,874 A | 4/1997 | Baran | 128/753 |
| 5,623,241 A | 4/1997 | Minkoff | 335/296 |
| 5,660,180 A | 8/1997 | Malinowski et al. | 128/660.03 |
| 5,682,897 A | 11/1997 | Pomeranz | 128/662.06 |
| 5,699,801 A | 12/1997 | Atalar et al. | 128/653.2 |
| 5,715,825 A | 2/1998 | Crowley | 128/602.06 |
| 5,728,079 A | 3/1998 | Weber et al. | 604/280 |
| 5,738,632 A | 4/1998 | Karasawa | 600/410 |
| 5,775,338 A | 7/1998 | Hastings | 128/898 |
| 5,792,055 A | 8/1998 | McKinnon | 600/410 |
| 5,833,608 A | 11/1998 | Acker | 600/409 |
| 5,833,632 A | 11/1998 | Jacobsen et al. | 600/585 |
| 5,840,031 A | 11/1998 | Crowley | 600/440 |
| 5,868,674 A | 2/1999 | Glowinski et al. | 600/410 |
| 5,916,162 A | 6/1999 | Snelten et al. | 600/411 |
| 5,928,145 A | 7/1999 | Ocali et al. | 600/410 |
| 5,938,609 A | 8/1999 | Pomeranz | 600/439 |
| 5,938,692 A | 8/1999 | Rudie | 607/101 |
| 5,964,705 A | 10/1999 | Truwit et al. | 600/423 |
| 5,968,052 A | 10/1999 | Sullivan, III et al. | 606/108 |
| 6,004,269 A | 12/1999 | Crowley et al. | 600/439 |
| 6,011,995 A | 1/2000 | Guglielmi et al. | 607/99 |
| 6,019,737 A | 2/2000 | Murata | 600/585 |
| 6,026,316 A | 2/2000 | Kucharczyk et al. | 600/420 |
| 6,031,375 A | 2/2000 | Atalar et al. | 324/307 |
| 6,032,078 A | 2/2000 | Rudie | 607/101 |
| 6,051,974 A | 4/2000 | Reisker et al. | 324/318 |
| 6,058,323 A | 5/2000 | Lemelson | 600/408 |
| 6,061,587 A | 5/2000 | Kucharczyk et al. | 600/411 |
| 6,104,943 A | 8/2000 | Frederick et al. | 600/410 |
| 6,171,240 B1 | 1/2001 | Young et al. | 600/410 |
| 6,233,474 B1 | 5/2001 | Lemelson | 600/411 |
| 6,263,229 B1 | 7/2001 | Atalar et al. | 600/423 |
| 6,306,132 B1 | 10/2001 | Moorman et al. | 606/41 |
| 6,377,837 B1 | 4/2002 | Coutts et al. | 600/423 |
| 6,549,800 B1 | 4/2003 | Atalar et al. | 600/423 |
| 2001/0056232 A1 | 12/2001 | Lardo et al. | 600/423 |
| 2002/0040185 A1 | 4/2002 | Atalar et al. | 600/169 |
| 2002/0045816 A1 | 4/2002 | Atalar et al. | 600/423 |
| 2003/0028095 A1 | 2/2003 | Tulley et al. | 600/422 |
| 2004/0199071 A1 | 10/2004 | Lardo et al. | |

FOREIGN PATENT DOCUMENTS

| | | |
|---|---|---|
| EP | 0 557 127 A2 | 8/1993 |
| EP | 0673621 A1 | 9/1995 |
| EP | 0 557 127 A3 | 3/1996 |
| JP | 61994 -70902 | 3/1994 |
| WO | WO 98/52461 | 11/1998 |
| WO | WO 99/27390 | 6/1999 |
| WO | WO 00/64003 | 10/2000 |

OTHER PUBLICATIONS

Lardo, "Real-Time Magnetic Resonance Imaging: Diagnostic and Interventional Applications" *Pediatr Cardiol* 21:80,98,2000.

Atalar et al.;"High Resolution Intravascular MRI and MRS using a Catheter Receiver Coil,", Magnetic Resonance in Medicine, 36:596-605 (1996).

Edelman et al.; "Magnetic Resonance Imaging" NEJM. 328: 708-716 (1993).

Farmer et al.;"Implanted Coil MR Microscopy of RenalPathology", Magn. Reson. Med., 10: 310-323 (1989).

Garwood et al.;"Magnetic Resonance Imaging with Adiabatic Using a Single Surface Coil for RF Transmission and Signal Detection", Magnetic Resonance in Medicine 9: 25-34 (1989).

Hoult et al.;"The Signal-to-Noise Ratio of the Nuclear Magnetic Resonance Experiment" J. Magn. Reson., 24: 71-85 (1976).

Hoult; "Rotating Frame Zeugmatography", Phil. Trans. R. Soc. Lond. B. 289: 543-547 (1980).

Jolesz et al.; "Interventional Magnetic Resonance Therapy", Seminars in Interventional Radiology, 12: 20-27 (1995).

Ocali et al.; "Intravascular Magnetic Resonance Imaging Using a Loopless Catheter Antenna", MRM, 37: 112-118 (1997).

Silverman et al.; "Interactive MR-guided Biopsy in an Open configuration MR Imaging System", Radiology, 197: 175-181 (1995).

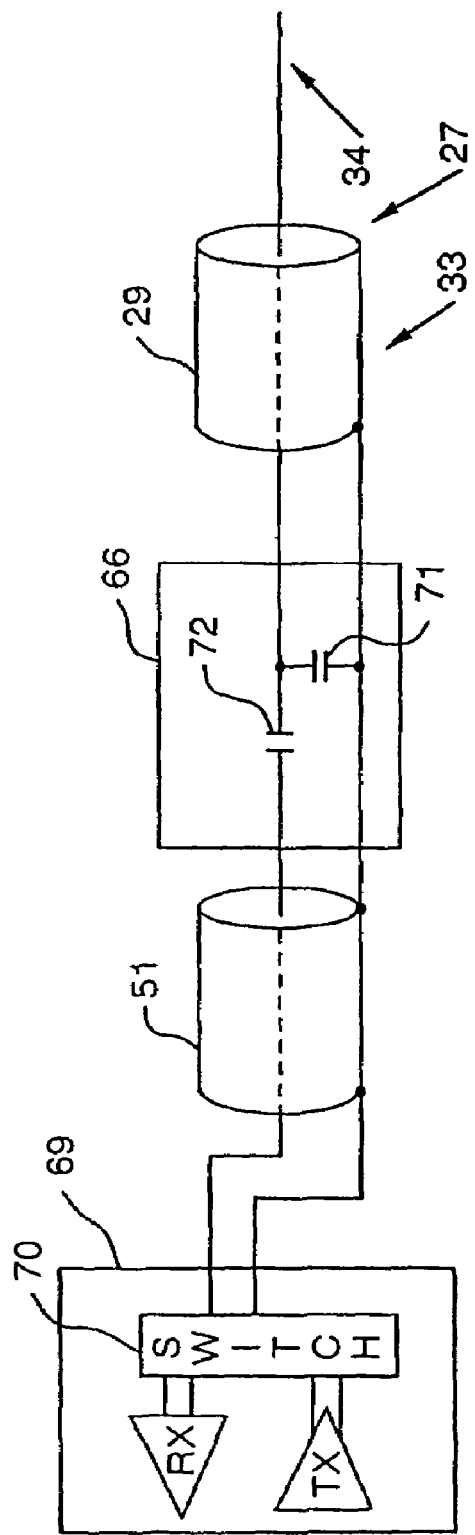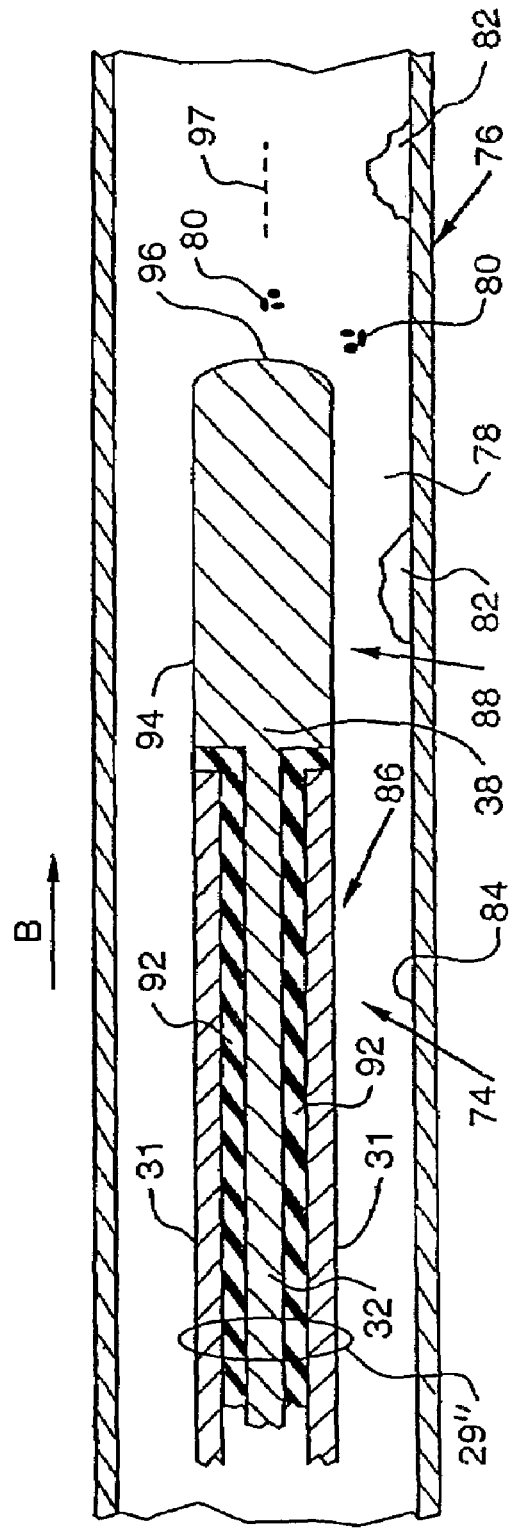

BIOPSY AND SAMPLING NEEDLE ANTENNAS FOR MAGNETIC RESONANCE IMAGING-GUIDED BIOPSIES

CROSS-REFERENCE TO RELATED APPLICATIONS

This application is a continuation-in-part of U.S. patent application Ser. No. 09/360,144, filed Jul. 26, 1999, now abandoned, which is a continuation-in-part of U.S. patent application Ser. No. 08/638,934, filed Apr. 25, 1996, now U.S. Pat. No. 5,928,145. This application also claims benefit of priority to U.S. Provisional Patent Application Ser. No. 60/286,271, filed Apr. 5, 2001, entitled "Biopsy Needle Antenna for MR Guided Biopsies." The aforementioned applications are incorporated herein in their entireties by this reference.

FIELD

The disclosed systems and methods relate to magnetic resonance imaging antennas, and in some embodiments to magnetic resonance imaging antennas adapted for use as biopsy or sample needles.

BACKGROUND

The advantageous use of magnetic resonance technology in providing safe, rapid images of a patient has long been known. It has also been known to employ magnetic resonance technology in producing chemical shift spectra to provide information regarding the chemical content of a material.

In a general sense, magnetic resonance imaging involves providing bursts of radio frequency energy on a specimen positioned within a main magnetic field in order to induce responsive emission of magnetic radiation from the hydrogen nuclei or other nuclei. The emitted signal may be detected in such a manner as to provide information as to the intensity of the response and the spatial origin of the nuclei emitting the responsive magnetic resonance signal. In general, imaging may be performed in a slice or plane, in multiple planes, or in a three-dimensional volume with information corresponding to the responsively emitted magnetic radiation being received by a computer which stores the information in the form of numbers corresponding to the intensity of the signal. The pixel value may be established in the computer by employing Fourier Transformation which converts the signal amplitude as a function of time to signal amplitude as a function of frequency. The signals may be stored in the computer and may be delivered with or without enhancement to a video screen display, such as a cathode-ray tube, for example, wherein the image created by the computer output will be presented through black and white presentations varying in intensity, or through color presentations varying in hue and intensity. See, generally, U.S. Pat. No. 4,766,381.

One of the beneficial end uses of the disclosed systems and methods is in connection with atherosclerotic disease which is a major cause of mortality and morbidity in the United States. Localized forms of the disease, such as the deposit of plaque on the walls of blood vessels, can restrict local blood flow and require surgical intervention in some instances. While angiography is an effective means for detecting the luminal narrowing caused by plaque, it does not provide information regarding the nature of the process leading to blood flow reduction. Unfortunately, therapeutic methods, such as intravascular intervention, may experience failure due to the lack of sufficiently precise imaging methods. An imaging system capable of providing detailed, qualitative and quantitative data regarding the status of vascular walls at the time of surgical intervention, could favorably influence the outcome by enabling the selection of the intervention method to be customized to the particular need. It would also serve to provide precise guidance for various forms of localized therapy.

It has been known to use angioplasty and intravascular ultrasound for imaging plaques. See, generally, Spears et al., "In Vivo Coronary Angioscopy," *Journal of the American College of Cardiology*, Vol. 1, pp. 1311–14 (1983); and Waller et al., "Intravascular Ultrasound: A Histological Study of Vessel During Life," *Circulation*, Vol. 85, pp. 2305–10 (1992). Intravascular ultrasound, however, provides several drawbacks, including the insensitivity to soft tissue and the inability to reliably detect thrombus and discriminate thrombus (new or organized) superimposed upon plaque from soft lipid-laden plaques. Also, the presence of artifacts related to transducer angle relative to the vessel wall, and an imaging plane limited to the aperture of the transducer in variable resolution at different depths of view are further problems with this approach.

The feasibility of identification of atherosclerotic lesions by employing magnetic resonance (MR) microimaging in vitro has previously been suggested. See, for example, Pearlman et al., "Nuclear Magnetic Resonance Microscopy of Atheroma in Human Coronary Arteries," *Angiology*, Vol. 42, pp. 726–33 (1991); Asdente et al., "Evaluation of Atherosclerotic Lesions Using NMR Microimaging," *Atherosclerosis*, Vol. 80, pp. 243–53 (1990); and Merickel et al., "Identification and 3-d Quantification of Atherosclerosis Using Magnetic Resonance Imaging," *Comput. Biol. Med.*, Vol. 18, pp. 89–102 (1988).

It has also been suggested that MRI can be used for quantification of atherosclerosis. See, generally, Merickel et al., "Noninvasive Quantitative Evaluation of Atherosclerosis Using MRI and Image Analysis," *Arteriosclerosis and Thrombosis*, Vol. 13, pp. 1180–86 (1993).

Yuan et al., "Techniques for High-Resolution MR Imaging of Atherosclerotic Plaques," *J. Magnetic Resonance Imaging*, Vol. 4, pp. 43–49 (1994) discloses a fast spin echo MR imaging technique to image atherosclerotic plaques on an isolated vessel that has been removed by carotid endarterectomy. As the signal-to-noise ratio (SNR) decreases with the decrease in imaging time and increase in resolution, special radio frequency (RF) receiver coils were designed. The article suggests that by the use of special MR hardware at 1.5 T using various T1 and T2-weighted pulse sequences, it is possible to discriminate foam cells, fibrous plaque organized thrombus, new thrombus, loose necrosis and calcium.

It has also been suggested that the fat content of atherosclerotic plaque in excised tissue samples can be determined using chemical shift imaging or chemical shift spectroscopy. See, generally, Vinitski et al., "Magnetic Resonance Chemical Shift Imaging and Spectroscopy of Atherosclerotic Plaque," *Investigative Radiology*, Vol. 26, pp. 703–14 (1991); Maynor et al., "Chemical Shift Imaging of Atherosclerosis at 7.0 Tesla," *Investigative Radiology*, Vol. 24, pp. 52–60 (1989); and Mohiaddin et al., "Chemical Shift Magnetic Resonance Imaging of Human Atheroma," *Br. Heart J.*, Vol. 62, pp. 81–89 (1989).

The foregoing prior art articles in the aggregate could lead one skilled in the art to conclude that MR, while having potential for fully characterizing vessel wall disease, suffers from low anatomic resolution unless used in vitro on small specimens with high resolution methods.

It is known that in order to obtain the desired high-resolution imaging and spectroscopy of arteriosclerotic plaques, a coil can be placed close to the target blood vessel.

In Kantor et al., "In vivo $^{31}$P Nuclear Magnetic Resonance Measurements in Canine Heart Using a Catheter-Coil," *Circulation Research*, Vol. 55, pp. 261–66 (August 1984), there is disclosed an effort to improve the SNR in the $^{31}$P spectroscopy of a dog myocardium using an elliptical coil. This coil is rigid, rather bulky, and designed for spectroscopy of the myocardium, but is not ideal for vessels.

Disclosures of efforts to develop catheter coils for imaging vessel walls are contained in Martin et al., "MR Imaging of Blood Vessel with an Intravascular Coil," *J. Magn. Reson. Imaging*, Vol. 2, pp. 421–29 (1992); and Hurst et al., "Intravascular (Catheter) NMR Receiver Probe: Preliminary Design Analysis and Application to Canine Iliofemoral Imaging," *Magn. Reson. Med.*, Vol. 24, pp. 343–57 (April 1992). These disclosures employ two tiny diameter, back-to-back solenoid coils to produce a good axial profile when the coils are placed along the main magnetic field.

Martin et al., "Intravascular MR Imaging in a Porcine Animal Model," *Magn. Reson. Med.*, Vol. 32, pp. 224–29 (August 1994) discloses use of the system disclosed in the above-cited Martin et al. article for high-resolution images of live animals. See, also, Abstract, McDonald et al., "Performance Comparison of Several Coil Geometries for Use in Catheters," RSNA 79th Scientific Meeting, *Radiology*, Vol. 189(P), p. 319 (November 1993). A strong disadvantage of these disclosures is that multislice acquisition cannot be carried out because the longitudinal coverage of the sensitive regions is limited to a few millimeters. Furthermore, the coil itself does not have the desired flexibility while maintaining the desired efficiency of data acquisition.

U.S. Pat. No. 5,170,789 discloses a nuclear magnetic resonance (NMR) coil probe, in the form of a loop, that is said to be insertable within a specimen, which has an opening, for purposes of nuclear magnetic resonance spectroscopy (NMRS). The disclosed two component probe, which is in the nature of an endoscope to examine the colon or cervix, has a first portion which is insertable into a body cavity and a second portion which is external to such cavity. The probe has a flexible coil body with an oval or circular shape that may deform during insertion. As a result, the coil may require tuning after insertion. If the coil were made of a very rigid material, insertion problems may occur. Also, a tuning and matching circuit, in the external portion, may limit the depth of insertion.

U.S. Pat. No. 4,932,411 discloses a probe with a transmit/receive coil for insertion in channels which are surgically or otherwise inserted in body organs, such as the brain, liver or kidneys. The coil, which is in the form of a loop, is carried and wound on the distal end of a carrier which is used to insert the coil into the body channel.

U.S. Pat. No. 4,672,972 discloses an NMR probe disposed at the distal end of a catheter or endoscope for obtaining NMR spectra from within a patient. The multi-turn probe has a parametric amplifier and/or a gate-array attached to it and, also, has a coil cooling system.

U.S. Pat. No. 5,413,104 discloses an invasive MRI transducer having a balloon, at least one lumen, and a flexible coil loop for insertion in a body cavity.

It has been known to employ an MR-active invasive device with RF transmitter coils for selective MR angiography of blood vessels. See, generally, U.S. Pat. No. 5,447,156.

It has also been known to employ an intravascular catheter with a Faraday screen to prevent RF electric-field interactions with the sample, such as blood, which cause the coil to detune. See, generally, U.S. Pat. No. 5,419,325.

MR compatibility characteristics of various catheter and guide wire systems, for use in interventional MR procedures, has been considered. See Dumoulin et al., "Real-time Position Monitoring of Invasive Devices Using Magnetic Resonance," *Magnetic Resonance in Medicine*, Vol. 29, pp. 411–15 (March 1993); and Abstract, Koechli et al., "Catheters and Guide Wires for Use in an Echo-planar MR Fluoroscopy System," RSNA 79th Scientific Meeting, *Radiology*, Vol. 189(P), p. 319 (November 1993).

McKinnon et al., "Towards Visible Guidewire Antennas for Interventional MRI," *Proc. Soc. Mag. Res.*, Vol. 1, p. 429 (August 1994) discloses antenna designs which are asserted to make guidewires, biopsy or sample needles and other vascular interventional devices visible by MRI. One MRI stub antenna is a length of coaxial cable with 10 cm of the braid removed from the end. One end of the coaxial cable is directly connected to the surface coil input of an MRI scanner and the other end is placed in a water filled phantom. The MR image is a bright line corresponding to spins in the immediate neighborhood of the cable. A preferred MRI stub antenna is an unterminated twisted pair cable having a diameter of 0.2 or 1 mm, and a corresponding image line width of 1 or 3 mm, respectively, which provides a finer image than the coaxial cable stub antenna. A preferred combination is a steerable guidewire containing a twisted pair cable. It is suggested that a surface coil could be used simultaneously with a guidewire antenna by combining, as with phased array coils, the specimen image from the surface coil with the image of the stub antenna using the data acquired from the stub antenna, to localize the in vivo device during interventional MRI.

It has been known to employ an invasive device having an RF coil for transmitting RF signals which are detected by external RF receive coils to track the invasive device. See, generally, U.S. Pat. No. 5,437,277.

It has also been known to employ external RF transmitter/receiver coils. See, generally, U.S. Pat. No. 5,447,156.

U.S. Pat. No. 5,323,778 discloses a probe for insertion in an artery or other body passageway. The probe has an MRI coil, an external MRI RF source and an RF heating apparatus for hyperthermia therapy.

Japanese Kokai Patent Application No. Hei 6[1994]-70902 to Koshiichi (hereinafter "Koshiichi") discloses two forms of dipole antenna. The first form has four wires and three ends. Two input leads are provided and two conducting poles form the dipole. One pole is inserted into a body cavity while the other is outside the body. The length of the inserted pole is about 1.2 meters at the field strength of 1.5 T common to many whole-body MRI systems today, resulting in a total antenna dipole length of about 2.4 meters. This three-ended dipole is impractical and/or has major practical disadvantages because i) the pole length is too long for applications to body cavities, blood vessels, etc.; ii) the inserted pole is loaded by the body impedance to an extent which varies with the length inserted, resulting in the MRI resonant frequency and match impedance varying with the length of insertion; iii) the fact that one end is inserted and the other end is not results in imbalancing of the impedance of the dipole which could deleteriously affect safety and performance; iv) because the length of the poles is comparable to the input leads, the tuning of the MRI resonant frequency and the impedance matching of the coil will depend on the location, orientation, and bending of each pole relative to the other; v) because the pole length is so long (about 1.2 meters at 1.5 T) this MRI probe will perform poorly compared to preexisting MRI coils whose dimensions are smaller, rendering it a disadvantageous probe design relative to pre-existing MRI probe technologies, including ones designed for use external to the body (such as solenoid "bird cage" MRI coils, surface coils, etc.); and vi) it is impractical to maintain an orientation of the dipole relative to the magnetic field when such coil is introduced into the convoluted and contorted passages of the body. For these reasons, the first dipole antenna design of Koshiichi has significant impediments for human applications.

Koshiichi further describes a second embodiment of his probe wherein one of the poles is folded back and incorporated into a sleeve. While this may partially overcome the problem of having a free end, the other problems discussed above with respect to his first embodiment remain. In particular, the 2.4 meter length is excessively long, has inferior performance with respect to existing MRI probes which do not allow insertion, and the end with the single pole will interact with the sleeved end containing the other pole and the input leads, making it impractical to tune.

U.S. Pat. No. 5,358,515 discloses a microwave hyperthermia applicator for limited heating of cancerous tissue including upper and lower dipole halves of the same diameter. The upper dipole half is a widened metal extension of the inner conductor of an insulated coaxial cable. The lower dipole half is a metal cylinder connected to the outer sheath of the coaxial cable. A π/2(λ/4) transformer, such as the outermost metal cylindrical sheath of a triaxial cable, is separated at its upper end from the lower dipole half which is connected to the coaxial cable outer sheath. The transformer is filled with a dielectric medium and is connected at its lower end to such coaxial cable outer sheath. When the antenna is inserted in a dissipative medium and supplied with microwave energy through the coaxial cable, only that area of the medium immediately around the antenna is heated.

MRI has many desirable properties for the diagnosis and therapy of atherosclerotic disease. For example, it is possible to see lesions directly, even before the plaques calcify. However, the SNR of MR images obtained from conventional surface or body coils is insufficient. This is because the coils placed outside the body pick up noise from a very large region of the body. To achieve satisfactory quality, the signal receiver can be placed as close as possible to the tissue of interest (e.g., blood vessels). A coil placed on the tip of a catheter and inserted into the blood vessels could be a solution; but, the real part of the impedance of a catheter coil is relatively small and, hence, a tuning and matching circuit is preferably located immediately after the coil within the blood vessels. It is believed that prior art designs that do otherwise suffer from a significant SNR loss. On the other hand, it is believed that prior art designs, which have a tuning and matching circuit immediately after the coil in blood vessels, are too thick to be placed into small vessels.

There remains, therefore, a very real and substantial need for an improved apparatus and method for MR imaging and spectroscopic analysis of specimens in a manner which provides efficient data acquisition with maximum SNR while permitting in vivo or in vitro acquisition from small vessels and a wide range of other types of specimens.

SUMMARY

As used herein, the term "specimen" shall refer to any object other than a loopless antenna placed in the main magnetic field for imaging or spectroscopic analysis and shall expressly include, but not be limited to members of the animal kingdom, including humans; test specimens, such as biological tissue, for example, removed from such members of the animal kingdom; and inanimate objects or phantoms which may be imaged by magnetic resonance techniques, or which contain water or sources of other sensitive nuclei.

As used herein, the term "loopless antenna" shall expressly include, but not be limited to a dipole antenna and any and all equivalents thereof, such as, for example, a dipole antenna having two poles at least one of which includes a mechanical loop (see, e.g., FIG. 14).

As used herein, the term "patient" shall mean human beings and other members of the animal kingdom.

As used herein, the term "composite image" shall mean a magnetic resonance image that is formed from magnetic resonance data obtained by a magnetic resonance antenna and a magnetic resonance scanner, body coil, or surface coil. The data from the magnetic resonance antenna and the magnetic resonance scanner, body coil, or surface coil may be obtained simultaneously or substantially simultaneously. An image formed by a biopsy or sampling needle antenna can preferably be a high resolution image, such as one millimeter resolution, submillimeter resolution, 300 micron resolution, 100 micron resolution, or 10 micron resolution.

In an embodiment, a biopsy or sample needle antenna includes a magnetic resonance imaging antenna, having an outer shield, and an inner conductor electrically insulated from the outer shield by a dielectric; and a biopsy or sample needle electrically connected to the inner conductor and electrically insulated from the outer shield by the dielectric.

In an embodiment, a biopsy needle antenna may include a cannula being formed at least in part of a conductive material, an obturator being formed at least in part of a conductive material, the obturator being slideably displaceable relative to the cannula, an insulator electrically insulating the cannula from the obturator, and a connector that can couple the cannula and the obturator to a magnetic resonance interface circuit.

In an embodiment, a sampling needle antenna may include a cannula being formed at least in part of a conductive material, an obturator being formed at least in part of a conductive material, the obturator being slideably displaceable relative to the cannula, and an insulator electrically insulating the cannula from the obturator, wherein the outer shield, the inner conductor, and the insulator form a magnetic resonance imaging antenna.

In an embodiment, a method of obtaining a sample with magnetic resonance imaging guidance can include providing a sampling needle magnetic resonance imaging antenna, advancing the antenna to a structure from which the sample is to be taken, detecting magnetic resonance data by the antenna, and coupling the sample to the antenna. In an embodiment, a sample can be a biopsy.

In an embodiment, a biopsy or sample needle antenna can include a cannula being formed at least in part of a conductive material, an obturator being formed at least in part of a conductive material, the obturator being slideably displaceable within the cannula, and an insulator electrically insulating the cannula from the obturator, wherein the outer shield, the inner conductor, and the insulator form a magnetic resonance imaging antenna.

In an embodiment, a magnetic resonance imaging antenna can include an inner conductor, an outer shield slideably displaceable with respect to the inner conductor, and an insulator electrically insulating the inner conductor from the outer shield.

In an embodiment, a method of obtaining a magnetic resonance imaging-guided biopsy can include providing a biopsy or sample needle magnetic resonance imaging antenna, advancing the antenna to a structure from which the biopsy is to be taken, detecting magnetic resonance data by the antenna, coupling the biopsy to the antenna.

In an embodiment, a method of obtaining a magnetic resonance imaging-guided biopsy can include providing a biopsy or sample needle antenna, having a magnetic resonance imaging antenna, including an outer shield, and an inner conductor electrically insulated from the outer shield by a dielectric, and a biopsy or sample needle electrically connected to the inner conductor and electrically insulated from the outer shield by the dielectric; advancing the needle to a lesion, imaging the lesion with the antenna, and taking a sample of the lesion with the needle.

An embodiment may further comprise a sheath, the biopsy or sample needle being slideably displaceable within the sheath. In an embodiment, the sheath can be defined by the outer shield.

In an embodiment, at least one of the outer shield, the inner conductor, and the biopsy or sample needle can include at least one of a magnetic resonance compatible material, gold, sliver, copper, aluminum, gold-silver, gold-copper, silver-copper, platinum, and platinum-copper.

In an embodiment, the outer shield and the inner conductor can form a coaxial cable. In an embodiment, the coaxial cable may be electrically interconnected to an impedance matching circuit.

In an embodiment, at least one of the outer shield, the inner conductor, and the biopsy or sample needle can include at least one of a superelastic material, platinum, iridium, MP35N, tantalum, Nitinol, L605, gold-platinum-iridium, gold-copper-iridium, titanium, and gold-platinum.

In an embodiment, the outer shield can be slideably displaceable with respect to the inner conductor. In an embodiment, the inner conductor can include an obturator and the outer shield comprises a cannula slideably displaceable over the obturator. In an embodiment, the obturator can further include a side-slit. In an embodiment, the cannula can include a distal end having a cutting edge, the cutting edge slideably displaceable over the side-slit. In an embodiment, the cannula can cover at least the side-slit.

In an embodiment, the cannula can be spring-loaded. In an embodiment, at least a portion of the obturator can protrude from a distal end of the cannula. An embodiment can further include a spring coupled to the outer shield. In an embodiment, the spring can be electrically coupled to the outer shield.

In an embodiment, the dielectric can include at least one of flurorethylene polymer, tetrafluoroethylene, polyester, polyethylene, silicone, metal oxide, glass, and polyethylene terephthalate. In an embodiment, the dielectric can be covered by a lubricious coating. In an embodiment, the lubricious coating can include at least one of polyvinylpyrrolidone, polyacrylic acid, and silicone.

In an embodiment, the inner conductor and outer shield can be electrically coupled to an interface. In an embodiment, the interface can include at least one of a tuning-matching circuit, a balun circuit, a decoupling circuit, and a variable capacitor. In an embodiment, the interface can couple to an MRI scanner.

In an embodiment, the biopsy or sample needle antenna can receive magnetic resonance spectroscopy information from a sample. Magnetic resonance spectroscopy information can include, e.g., information from magnetic nuclei, such as hydrogen, phosphorus, sodium, and other known in the art. When a one-dimensional MR Spectroscopy technique along the length of the antenna is utilized, very high resolution spectroscopy of the tissue around the needle can be obtained. The antenna signal reception characteristics can facilitate localization, particularly in the radial direction. One use of a biopsy device disclosed herein is accurate localization of malignant tumors by using MR spectroscopy. It is known that at least some biopsy techniques have very high specificity but low sensitivity. On the other hand, some tumors may not be visible by hydrogen (proton) MRI, however proton or other nuclei, (such as Na, P, Ca etc) spectroscopy information may reveal signal that can differentiate the malignant tumor from the normal and the benign tumor. With the aid of the MR spectroscopy guidance, sensitivity of the biopsy procedure can be increased by placing the needle in the tumor with suspected malignancy.

In an embodiment, the antenna can include a cannula including an outer shield, an obturator including an inner conductor, the obturator slideably displaceable relative to the cannula, and an insulator electrically insulating the outer shield from the inner conductor.

In an embodiment, coupling can include trapping the biopsy between the cannula and the obturator. In an embodiment, trapping can include moving at least one of the cannula and the obturator relative to the other. An embodiment can further include coupling the magnetic resonance data to an MRI scanner to form a magnetic resonance image.

An embodiment provides a device that can be used as a biopsy or sample needle in MR-guided core biopsy procedures, as well as function as an MR antenna for accurate needle positioning and high-resolution imaging of the target. Such a device may have application in a number of MRI-guided diagnostic procedures to evaluate pathologic lesions including cancers, to assess the health of various organs in the body, and to provide information useful for assessing therapeutic response.

Systems and methods are disclosed to enhance and facilitate the performance of biopsy procedures with MRI.

In an embodiment, a biopsy device is MRI compatible.

In an embodiment, a biopsy device can be easily visualized and/or tracked by MRI.

An embodiment can facilitate high resolution imaging of a target area.

In an embodiment, a biopsy device permits sampling and collection of tissues and/or fluids under MRI guidance.

An embodiment provides an image-guided biopsy that obviates the need for biopsy needles that can generate visible artifacts for needle localization.

An embodiment provides a method to perform MRI-guided biopsy procedures.

An embodiment provides a system to perform MRI-guided biopsy procedures.

An embodiment provides for an MRI-compatible device that includes a biopsy needle, means for sampling and collection of tissue and fluid samples, and an antenna for receiving MRI signals. High resolution imaging of target lesions and tissues is rendered by virtue of the close proximity of the MRI antenna to the tissue of interest.

In an embodiment, an image may be a composite image.

An embodiment provides a device with an insulated movable obturator, which has a cutting edge that slices the tissue on the slide-slit portion and thus performs the biopsy procedure, collecting the tissue samples. The obturator also forms the inner conductor of a loopless antenna type detector (as described by Ocali and Atalar, cited above). In addition, the device is provided with a cannula, which, in conjunction with a mechanical spring assembly that is electrically connected to the cannula, effectively serves as the outer RF shield portion of the loopless antenna. The biopsy needle is charged, by drawing the plunger in the proximal direction. The MRI antenna receiver function is preferably performed with the biopsy needle charged and the obturator is pushed into the cannula.

In an embodiment, the biopsy needle MRI detector device is connected to circuitry that provides for decoupling of the antenna during MRI excitation, and for matching and tuning of the MRI antenna in order to enhance and maximize MRI performance. It also functions to connect the needle to an MRI scanner.

In an embodiment, a MRI-compatible biopsy needle device with MRI receiving antenna is combined with matching tuning and decoupling circuitry and an MRI scanner to guide, perform, and provide visualization of biopsy procedures.

An embodiment provides a method of performing an image-guided biopsy employing the MRI-compatible biopsy needle device with MRI receiving antenna, matching tuning and decoupling circuitry, in conjunction with an MRI scanner. The method provides for accurate needle positioning and high resolution imaging of target pathologic lesions and nearby tissues, thereby enabling avoidance of injury to critical areas as the device is introduced, and providing improved tissue characterization and morphologic information about suspected lesions and pathologies. This will facilitate potential medical interventions such as surgical planning, increase the accuracy of the biopsy procedure, and avoid unnecessary repeated biopsies.

An embodiment provides an MRI-compatible biopsy needle modified to form a loopless MRI antenna. The needle has a moveable cannula with a cutting edge that provides sample collection for subsequent removal and histological analysis. The needle device is interfaced to decoupling, matching and tuning circuit and connected to the receiver input of an MRI scanner, to permit images to be created from the MRI signals thereby detected. The images are used to guide the introduction and ingress of the biopsy needle into a subject positioned in the MRI scanner, for the purpose of providing accurate targeting of the biopsy site, and detailed imaging of the surrounding local anatomy for assessment.

In an embodiment, a method of MRI imaging includes positioning a specimen within a main magnetic field, introducing an antenna in close proximity to the specimen, employing as the antenna a loopless antenna, imposing the main magnetic field on a region of interest of the specimen, applying radio frequency pulses to the region of interest to excite magnetic resonance signals within the specimen, applying gradient magnetic pulses to the region of interest to spatially encode the magnetic resonance signals with the antenna receiving the magnetic resonance signals and emitting responsive output signals, employing processing means for receiving and processing the responsive output signals and converting them into magnetic resonance information, and employing display means for receiving the magnetic resonance information from the processing means and displaying the same as an image or as chemical shift spectra.

The antenna employed in one preferred embodiment has the loopless antenna and a coaxial cable means structured to be received within the intravascular system, the pancreatic duct, or a tortuous passageway of a patient.

The antenna employed in another preferred embodiment is a loopless antenna structured as a biopsy needle.

The antenna employed in another preferred embodiment has a balancing transformer means operatively associated with a portion of the outer shield of a coaxial cable. For applications within a blood vessel, an insulator in the balancing transformer is preferably employed with a dielectric constant about equal to a dielectric constant of blood in the blood vessel.

The antenna employed in another preferred embodiment has an impedance matching circuit electrically interposed between the loopless antenna and the processing means to enhance radio frequency power transfer and magnetic resonance signal-to-noise ratio from the loopless antenna to the processing means.

The antenna for most embodiments is preferably flexible so as to permit efficient movement through specimen passageways and other specimens or samples to be analyzed regardless of whether the path is straight or not.

The antenna may be employed in chemical shift imaging through acquisition of spatially localized chemical shift information.

In this manner, the method enables both imaging and chemical shift analysis which may also be advantageously employed substantially simultaneously with surgical intervention.

A dipole antenna portion of the loopless antenna may be on the order of about 3 cm to about 20 cm in length, and may have a relatively small maximum outer diameter of about 0.3 mm to about 1.0 cm.

In one embodiment, the antenna also functions as a transmitting antenna to provide the RF signals and, thereby, provide enhanced efficiency of operation for certain uses.

The method may also employ additional elements, such as a balancing transformer and/or an impedance matching circuit in order to provide enhanced operation.

A corresponding magnetic resonance analysis apparatus is provided.

A corresponding magnetic resonance antenna assembly includes an antenna having loopless antenna means at least for receiving magnetic resonance signals emitted from a specimen and emitting responsive output signals.

Disclosed systems and methods can facilitate providing high-resolution and spectroscopic imaging of the interior of specimens, including in vivo and in vitro imaging of patients and patient derived specimens or samples.

Disclosed systems and methods can facilitate rapid imaging of walls of small, tortuous blood vessels with high-resolution, as well as other specimens, and will permit the use of multislice data acquisition techniques.

Disclosed systems and methods can facilitate acquiring images simultaneously with surgical procedures such as removing plaque from blood vessels.

An embodiment includes a loopless, flexible antenna that can provide both qualitative and quantitative data and to facilitate use of the same substantially simultaneously with medical intervention to correct undesired conditions.

An embodiment facilitates acquiring morphological information about soft tissue and plaque.

An embodiment facilitates acquiring chemical information about soft tissue and plaque.

In an embodiment, the antenna may function only as a receiver antenna or may function as an antenna for both excitation and detection of MR signals.

In an embodiment, the antenna may function as an invasive probe, such as a catheter.

In an embodiment, the antenna may function as a probe-type medical device such as a biopsy needle.

In an embodiment, no tuning or impedance matching circuit is generally required.

In an embodiment, no tuning of the antenna is generally required after such antenna is inserted in a patient.

An embodiment can include or couple to an impedance matching circuit which may be employed with conventional hardware.

BRIEF DESCRIPTION OF THE FIGURES

FIG. 7 is a schematic illustration of the loopless antenna of FIG. 4, a matching circuit, two coaxial cables, and a transceiver.

FIG. 8 is a cross-sectional view of a loopless antenna and coaxial cable positioned in a blood vessel.

DESCRIPTION

Figure 1:
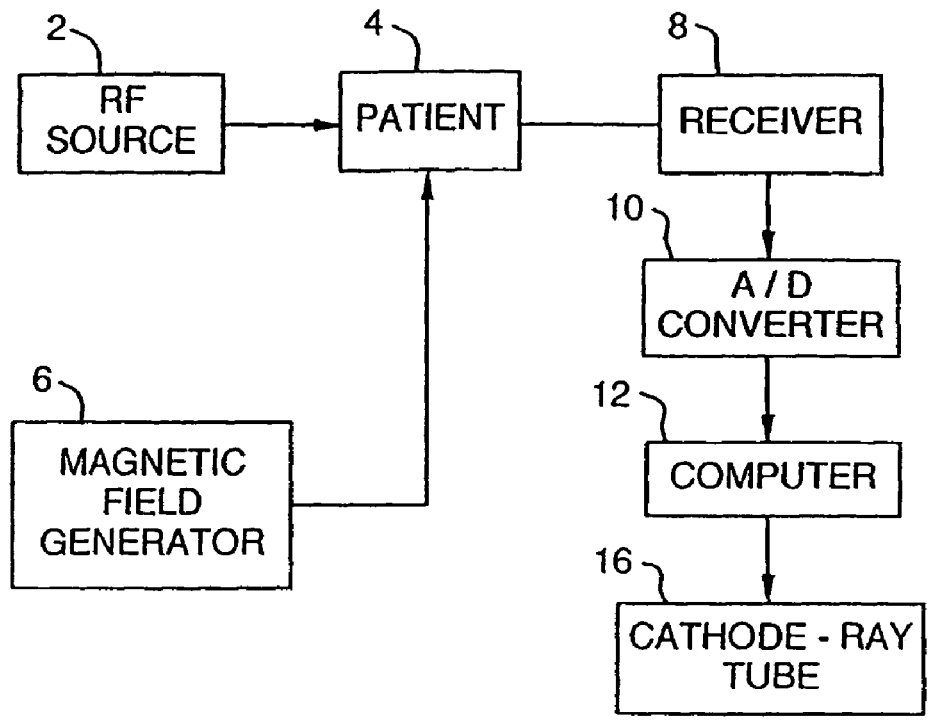
FIG. 1 is a schematic illustration of a magnetic resonance analysis system.

MRI-guided biopsies performed with non-magnetic devices using free-hand or stereotaxy techniques have been reported (see for example, S. G. Silverman et al., *Radiology*, 197:175–181, 1995; J. S. Lewin et al., *AJR Am J Roentgenol* 166:1337–1345,1996). These procedures also use artifacts generated by the needle for localization, and typically require the use of external MRI detection coils to determine the needle position and the target. Other needle designs, either coated or not coated with MRI detectable substances and manufactured from non-magnetic materials and appropriately protected from induced heating, can avoid MRI artifacts. However, even though such devices are MRI-compatible, because they are not deployed as MRI antennas themselves, they cannot contribute to MRI performance nor enable high-resolution MRI of the target area.

MRI signals are weak and the ability of an antenna to detect them depends on both the antenna size and its proximity to the source of those signals. Thus, in order to improve the MRI signal, an MRI antenna may be placed near or inside the subject to be imaged. Such improvements can enable valuable increases in resolution sensitivity of a target area, reduction in scan time, and provide evidence of the MRI antenna itself on the MRI. For example, long, flexible loop antennas produce local regions of high signal permitting high resolution MRI in their vicinity when implemented as an internal MRI antenna, as shown for example by Atalar E, Bottomley P A, Ocali O, Correia L C, Kelemen M D, Lima J A, Zerhouni E A, "High resolution intravascular MRI and MRS by using a catheter receiver coil", *Magn Reson Med.* 1996;36:596–605. The loopless antenna design of Ocali O and Atalar E ("Intravascular magnetic resonance imaging using a loopless catheter antenna" in *Magn Reson Med.* 1997;37:112–8) may also be deployed as an internal MRI antenna to realize important resolution and sensitivity advantages.

By providing the ability both to visualize where on the image the antenna is located, and to provide high sensitivity and a high-resolution imaging capability an MRI scanner equipped with such detectors could be advantageous in medical procedures where MRI is used simultaneously to track the position of an interventional device, and to provide a way of evaluating the structures surrounding the device. In particular, by developing MRI-compatible needle biopsy and/or needle interventional devices that incorporate an MRI antenna capability, needle biopsies and/or interventions could be performed under MRI guidance with the following important advantages over X-ray and ultrasound-guided needle techniques: (1) full 3D anatomical visualization of the organ or tissue of interest during the examination; (2) an ability to image in any plane or orientation; (3) MRI has much greater sensitivity to soft tissue and pathology, enabling superior characterization of pathologic features of a target region; (4) the ability to obtain diverse functional information about the target organ or tissue via one or more of the many available state-of-the-art MRI techniques; (5) MRI involves zero exposure to potentially damaging x-ray radiation; and (6) because localization is determined by the super-position of magnetic fields to which the body is transparent to, and not by beams, there are no beam diffraction and reflection artifacts, nor (7) problems with opacity or imaging though bone etc.

FIG. 1 shows a schematic representation of the general concept of magnetic resonance analysis as employed with a specimen. An RF source 2 provides pulsed radio frequency energy to the specimen to excite MR signals therefrom. The specimen, in the form shown, is a patient 4 disposed in the main magnetic field which is created by a magnetic field generator 6. The generator 6 includes a magnetic field gradient generator for establishing gradients in the main magnetic field by applying gradient magnetic pulses on the region of interest of the patient 4 in order to spatially encode the MR signals.

The exemplary patient 4 is generally aligned with the main magnetic field and the RF pulses are emitted perpendicular thereto to one portion, several portions, or all of the specimen. Where oblique imaging is employed, the angle of impingement of the vector representing the spatial gradient of the magnetic field will be angularly offset from either the x, y, or z directions (not shown). This arrangement results in excitation of the nuclei within the area or volume to be imaged and causes responsive emission of magnetic energy which is picked up by a receiver 8 having a loop antenna (i.e., a receiver coil) in close proximity to the patient 4.

Preferably, the loop antenna of the receiver 8 is aligned with the z direction (i.e., the direction of the main magnetic field) in order to have maximum sensitivity. In the event the loop antenna is perpendicular to the main magnetic field, it has a practically zero sensitivity at certain locations. For oblique angles therebetween, the loop antenna has data acquisition capability, albeit with reduced sensitivity, thereby permitting data acquisition even at oblique angles.

The loop antenna or receiver coil of the receiver 8 has a voltage induced in it as a result of such responsive emissions of magnetic energy. As a practical matter, separate coils or identical coils may be employed by the RF source 2 and receiver 8. The responsive output signal emerging from receiver 8 is amplified, phase-sensitive detected, and passes through analog-to-digital (A/D) converter 10 and enters a processor, such as computer 12, which receives and processes the signals from the converter 10 and creates MR information related thereto. Within computer 12 the Fourier Transformations of signals convert the plot of amplitude versus time to a map of the distribution of frequencies by plotting amplitude versus frequency. The Fourier Transformations are performed in order to establish the intensity value locations of specific image pixels of the specimen and to obtain chemical shift spectra at those locations. These values may be stored, enhanced or otherwise processed, and emerge to be received and displayed as an image or as chemical shift spectra, as appropriate, on a suitable screen, such as a cathode-ray tube (CRT) 16, for example.

In chemical shift spectra applications, for example, the magnetic field gradient generator of generator 6 generates the magnetic field gradient substantially parallel to the loop antenna of the receiver 8 over the region of interest in order to generate one-dimensional resolved chemical shift spectra which are spatially resolved substantially along the length of the loop antenna on the region of interest. The computer 12 converts spatially localized chemical shift information in the responsive output signals to chemical shift spectra, and employs the CRT 16 to receive and display such spectra. This facilitates one-dimensional chemical shift imaging in which the chemical shift information is spatially resolved in a direction substantially along the length of the loop antenna on the region of interest of the specimen.

Figure 2:
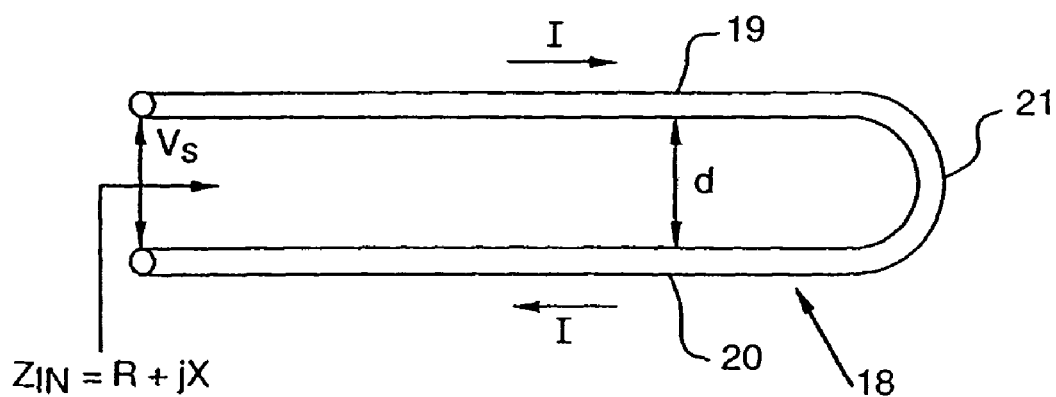
FIG. 2 is a form of a catheter coil for the system of FIG. 1.

Those skilled in the art will appreciate that the transmission properties of a coil may be used to analyze its reception properties. Referring to FIG. 2, in general, the signal voltage $V_S$ of a coil 18 is determined in Equation 1:

$$V_S = \omega \mu \vec{H} \cdot \vec{M} \qquad \text{(Eq. 1)}$$

wherein $\omega$ is $2\pi F$, F is frequency of RF source 2, $\mu$ is permeability constant, $\vec{H}$ is magnetic field (vector) generated by coil 18 at unit input current I, and $\vec{M}$ is sample magnetization (vector). Of the factors affecting the signal voltage $V_S$, H is the only coil-dependent parameter.

The RMS noise voltage $V_N$ of the coil 18 is determined in Equation 2:

$$V_N = \sqrt{4k_B T R f} \qquad \text{(Eq. 2)}$$

wherein $k_B$ is the Boltzman constant, T is sample temperature, R is real part of impedance seen from the terminals of coil 18, $f = 2BW/(N_x N_y NEX)$ is effective pixel bandwidth, BW is receiver bandwidth, $N_x$ is number of pixels along the readout direction, $N_y$ is number of pixels along the phase encoding direction, and NEX is number of averages. The only coil-dependent parameter that affects the noise voltage $V_N$ is R.

The signal-to-noise ratio (SNR) is determined in Equation 3:

$$SNR = \frac{V_S}{V_N} \propto \frac{H}{\sqrt{R}} \qquad \text{(Eq. 3)}$$

wherein, H is magnetic field (value) generated by coil 18 at unit input current I. To improve SNR, H should increase and R should decrease. For example, in coils, these are generally conflicting goals. A typical value of R for the coil 18 is about $0.5\Omega$.

In the structure of the conventional catheter coil 18, magnetic fields generated by the two conductors 19, 20 cancel partially. This cancellation effect becomes more pronounced as the distance of the specimen from the coil 18 increases. In this configuration, the path of the current I is completed by the end conductor 21, which forms an electrical loop or coil with the conductors 19, 20. The performance of the coil 18 depends strongly on the separation distance d between the conductors 19, 20 and worsens (improves) as such separation decreases (increases).

Figure 3:
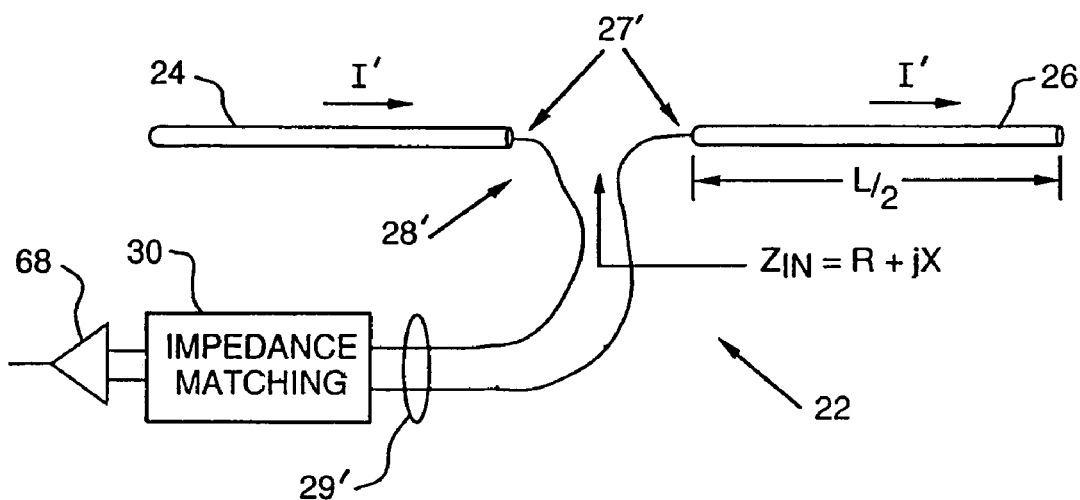
FIG. 3 is a schematic of a loopless antenna and an impedance matching circuit for the system of FIG. 1.

FIG. 3 illustrates an antenna 22. The cancellation of the magnetic fields is avoided by separating the conductors 24, 26 as schematically shown in FIG. 3. The H field increases considerably by this operation. In this configuration, the path of the current I' is not completed, and charges simply oscillate between the two tips of the antenna 22. The H field generated by the antenna 22 becomes circular thereabout and is approximately inversely proportional with the distance thereto. The antenna 22 includes the conductors 24, 26, which form a loopless antenna 27' having a dipole antenna portion 28' and a connection portion 29'; and, in this embodiment, an impedance matching circuit 30. The impedance matching circuit 30 is electrically interposed between the loopless antenna 27' and a preamplifier 68 of the receiver 8 of FIG. 1 and enhances RF power transfer and MR SNR from the antenna 27' to the converter 10 of FIG. 1. The parameters of the impedance matching circuit 30 are chosen to resonate the antenna 27' at the MR frequency of the nuclei of interest and to match the antenna 27' to the optimum input impedance of the preamplifier 68.

EXAMPLE 1

Figure 4:
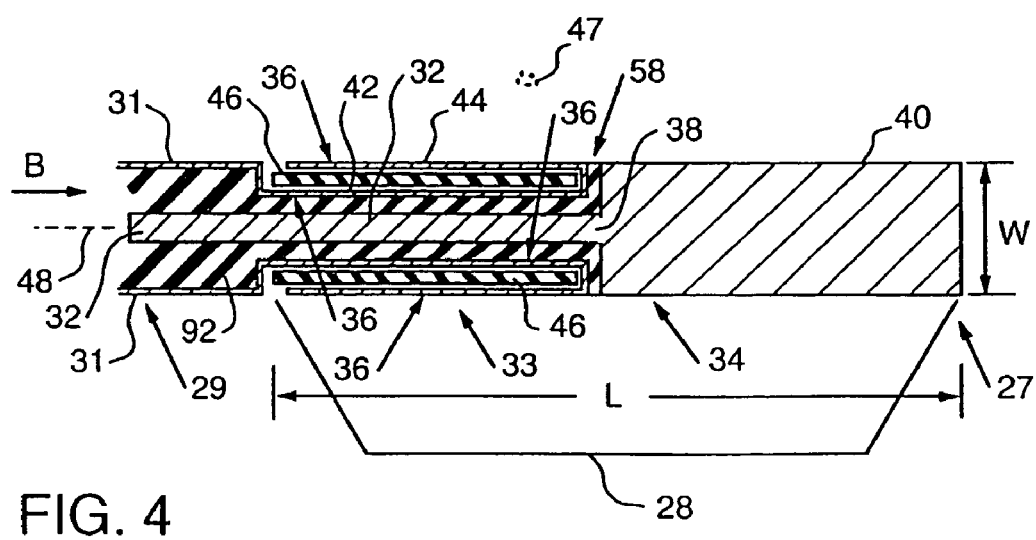
FIG. 4 is a cross-sectional view of a loopless balanced antenna.

FIG. 4 is a cross-sectional view of an exemplary loopless balanced antenna 27. A dipole antenna portion 28 receives MR signals emitted from a specimen responsive to pulsed RF signals and emits responsive output signals. A connection portion 29 emits the responsive output signals to the impedance matching circuit 30 of FIG. 3. In this embodiment, the connection portion 29 is a coaxial cable having an outer primary shield 31 and an inner conductor 32. The coaxial cable 29 is electrically interposed between the dipole antenna portion 28 and the impedance matching circuit 30.

The dipole antenna portion 28 has a first pole 33 and a second pole 34. A portion 36 of the outer shield 31 is operatively associated with the first pole 33. A portion 38 of the inner conductor 32 is operatively associated with the second pole 34. The second pole 34 preferably includes a cylindrical conductor 40 electrically interconnected with the portion 38 of the inner conductor 32.

The portion 36 of the outer shield 31 at the first pole 33 forms an inner primary shield 42 and an outer secondary shield 44, each of which is coaxial with the inner conductor 32. The first pole 33 includes the shields 42, 44. In this manner, the secondary shield 44 is also for receiving the MR signals.

The first pole 33 also includes a dielectric coating or insulator 46 under the outer secondary shield 44, between such shield 44 and the inner primary shield 42. The insulator 46 and the shields 42, 44 form a balancing transformer operatively associated with the first pole 33. The balancing transformer suitably disables current flow on the outer surface of the primary shield 31, without significantly impeding current flow on the inner surface thereof.

Preferably, the insulator 46 is a relatively high dielectric constant ($\in_r$) insulator having a value of about 70 to about 100. Preferably, for optimal balancing, the dielectric constant of the insulator 46 is selected in order that the length L/2 (as shown in FIG. 3) of the transmission line formed by the primary shield 42 and the secondary shield 44 (as shown in FIG. 4) has a length of $\lambda/4$, where $\lambda$ is the wavelength in the insulator 46 at the MR frequency of nuclei of interest. In this manner, the unbalanced current flowing on the outer surface of the primary shield 31 is greatly reduced.

For applications in vivo in a patient, the $\in_r$ value of the insulator 46 is preferably selected to match the $\in_r$ value of the surrounding medium 47 (e.g., the $\in_r$ value of blood which ranges from about 70 to about 100). For other applications, the antenna 27 is preferably introduced in close proximity to the specimen. The insulator 46 may be made of any insulator having a suitable $\in_r$ value and, preferably, is made of titanium oxide or a composite thereof.

Preferably, in terms of extending the sensitivity along the length of a loopless antenna, as discussed below in connection with FIG. 8, a balancing transformer is not employed. In the embodiment of FIG. 8, current flows on the outer surface of the primary shield 31 and the noise voltage is higher thereby providing a lower SNR. The primary shield 31 serves to receive the MR signal as well as the portion of the pole 86 which is adjacent the pole 88. However, removing the balancing transformer reduces the SNR slightly.

The balancing transformer of FIG. 4 is preferably employed to avoid unbalanced currents which would otherwise make the input impedance $Z_{IN}$ of FIG. 3 sensitive to changes in loading conditions and the position of the loopless antenna 27.

The inner conductor 32 and the cylindrical conductor 40 may be made of a good non-magnetic, electrical conductor, such as copper, silver, or skin effect, however, wherein only about an 8 μm outer layer of the conductors 32, 40 carries electrons at RF frequencies, a material plated with a good conductor will also function effectively. For example, silver plated copper, gold plated copper, or platinum plated copper may be employed.

The dipole antenna portion 28 of the exemplary balanced loopless antenna 27 has a length L of about 3 cm to about 20 cm, with larger (smaller) lengths obtained with smaller (larger) RF frequencies (e.g., less than about 400 MHz), although larger lengths of up to about 2 m are possible with the unbalanced loopless antenna 74 of FIG. 8. The length L facilitates multislice imaging without moving the loopless antenna 27. Preferably, resiliently flexible loopless antennas 27, 74 are provided. The optimal length of the antenna 27 at 1.5 T in human tissue is about 7 cm to about 10 cm. The exemplary balanced loopless antenna 27 has a maximum width W (FIG. 4) of about 0.5 mm to about 1.0 cm, although smaller widths of about 0.3 mm are possible with the unbalanced loopless antenna 74 of FIG. 8.

The sensitivity profile of the exemplary antennas 27, 74 depends on the respective antenna's orientation with respect to the main magnetic field. The best performance is achieved when the antennas 27, 74 are aligned with the main magnetic field. In other words, in order to function effectively, the longitudinal axis 48 is parallel to the main magnetic field B (FIGS. 4 and 8) with the poles 33, 34 along the length of the loopless antenna 27. For example, for in vivo applications of the antennas 27, 74, the patient (and, hence, the antenna therein), may be moved to provide suitable alignment with the direction of the main magnetic field B.

The antennas 27, 74 supply a relatively high signal voltage, since there are no magnetic field cancellations as in the coil 18 of FIG. 2. To estimate SNR performance, as shown in Equation 3, the noise resistance R (i.e., the real part of the impedance $Z_{IN}$) is necessary. The input impedance $Z_{IN}$ of the antennas 27, 74 may be measured experimentally (e.g., using a vector impedance meter in a saline solution which has conductivity similar to the particular specimen such as mammalian tissue). It is also possible to calculate the input impedance $Z_{IN}$ by solving the associated electromagnetic problem. Both the real (R) and imaginary (jX) parts of the input impedance $Z_{IN}$ are preferably employed in designing the impedance matching circuit 30 of FIG. 3.

Figure 5A:
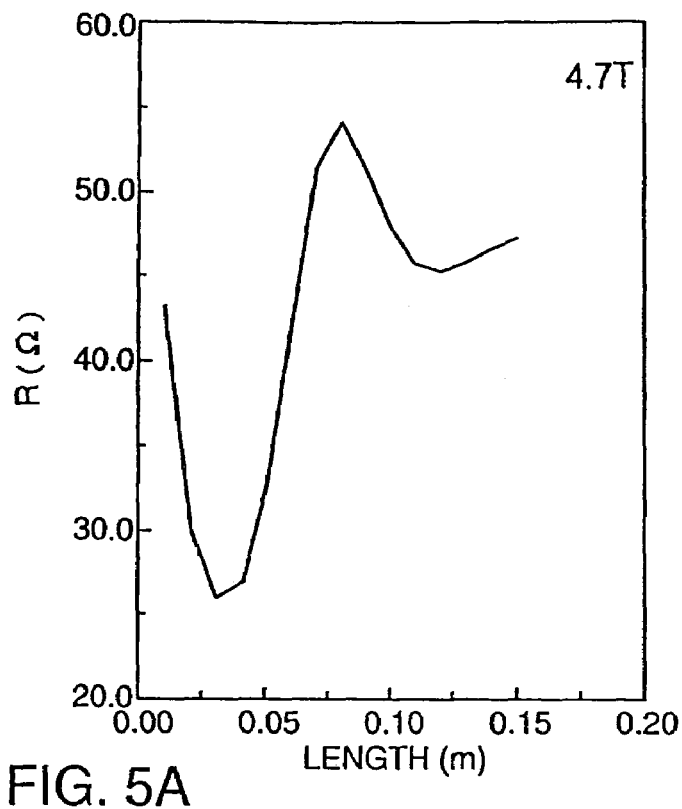
FIGS. 5A–5B are plots of noise resistance with respect to antenna length for a loopless antenna similar to the embodiment of FIG. 4.
Figure 5B:
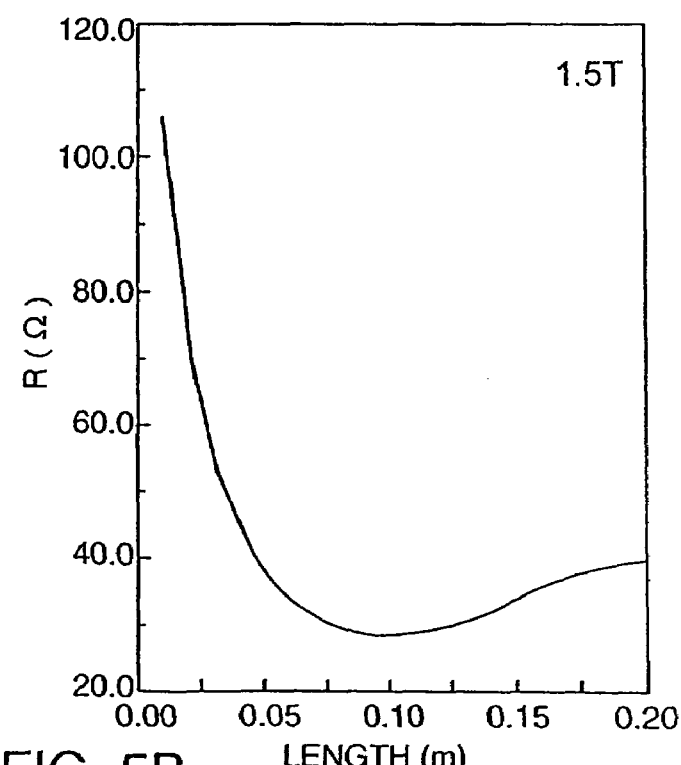

Preferably, for optimal SNR performance, the noise resistance R should be as small as possible. As shown in FIGS. 5A and 5B, noise resistance R (ohms) is plotted for changing antenna length (meters), for two different exemplary main magnetic field strengths, 4.7 Tesla (T) and 1.5 T, respectively, for a loopless antenna (not shown) similar to the loopless antenna 27 of FIG. 4. The loopless antenna represented by FIGS. 5A and 5B has a diameter of about 1.0 mm and a balancing transformer insulator with a dielectric constant ($\in_r$) representative of human body tissue. In both cases, R attains a shallow minimum (e.g., about 20Ω to about 30Ω). Preferably, the length of the loopless antenna is chosen around those minima.

The noise resistance R of the antenna 22 of FIG. 3 weakly depends on the radius of the conductors 24, 26. Compared to a typical 0.5Ω input impedance of the conventional coil 18 of FIG. 2, the noise resistance R of the loopless antenna 27 of FIG. 4 approaches about two orders of magnitude larger and, hence, the noise voltage $V_N$ approaches about one order of magnitude larger (as shown by the square root function of Equation 2). However, the signal voltage $V_S$ of the loopless antenna 27 is also larger. The SNR performances of the coil 18 and the loopless antenna 27 equate at a distance of about 5–8 times the conductor separation distance d for the coil 18. At smaller distances, the coil 18 is better, but for larger distances the loopless antenna 27 has a better SNR performance.

EXAMPLE 2

Figure 6:
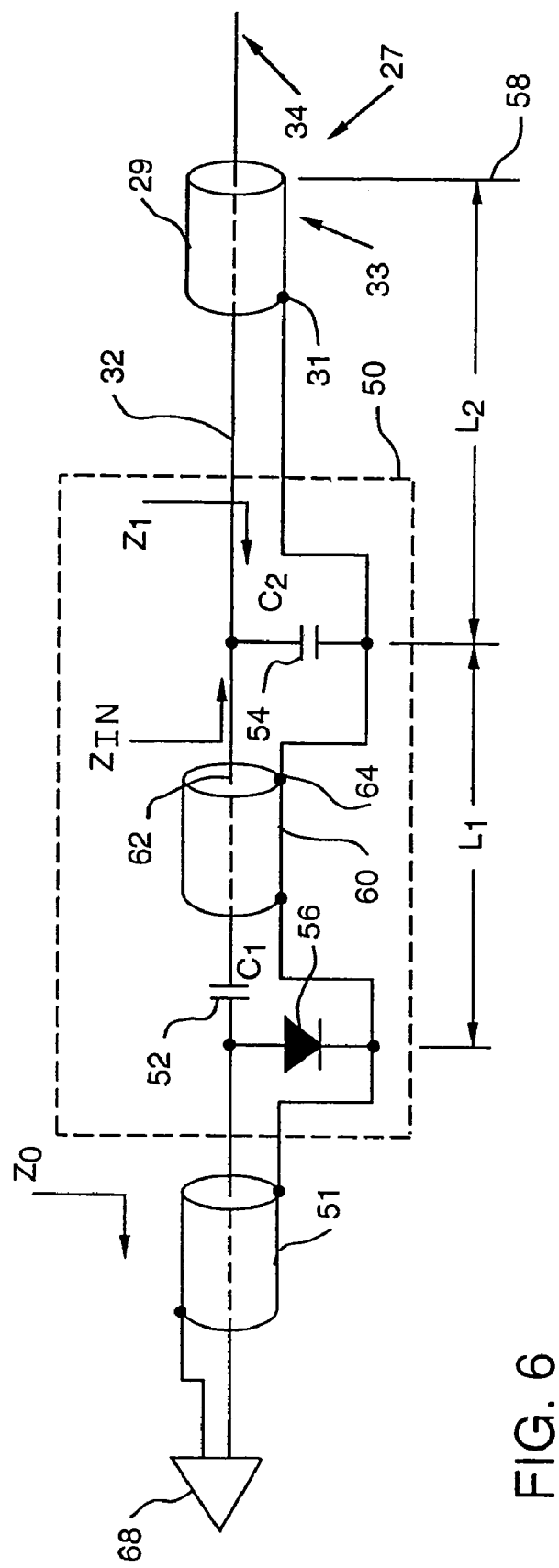
FIG. 6 is a schematic illustration of the loopless antenna of FIG. 4, an impedance matching and decoupling circuit, and a preamplifier.

FIG. 6 is a schematic illustration of the loopless antenna 27 of FIG. 4, and a suitable exemplary impedance matching and decoupling circuit 50, although the disclosed systems and methods are applicable to a wide variety of impedance matching circuits, and tuning and impedance matching circuits. The loopless antenna 27 is electrically interconnected to the circuit 50 by the coaxial cable 29. The circuit 50 serves to match the impedance of the loopless antenna 27 with the characteristic impedance $Z_0$ of a coaxial cable 51. The coaxial cable 51 is connected to the preamplifier 68 of the receiver 8 of FIG. 1 and carries the MR signal thereto. In this manner, the coaxial cable 51 is electrically interposed between the computer 12 of FIG. 1 and the circuit 50, with such circuit 50 matching the input impedance $Z_{IN}$ of the loopless antenna 27 to the characteristic impedance $Z_0$ of the cable 51.

The loopless antenna 27 has a relatively large noise resistance R, which makes it possible to place the circuit 50 relatively far from the antenna 27 without significant SNR performance degradation. This is an important advantage over the relatively low noise resistance coil 18 of FIG. 2 because, during imaging therewith, the matching circuitry (not shown) thereof is preferably placed inside the specimen to eliminate a significant SNR loss.

The circuit 50 includes a direct current (DC) blocking capacitor 52, a matching capacitor 54, and a PIN diode 56. The matching capacitor 54 is electrically interposed in the circuit 50 between the inner conductor 32 and the outer shield 31 of the coaxial cable 29. The PIN diode 56 is electrically interposed between the DC blocking capacitor 52 and the preamplifier 68. The DC blocking capacitor 52 is electrically interposed between the PIN diode 56 and the inner conductor 32 of the coaxial cable 29. The coaxial cable 29 is preferably structured with a suitable diameter for reception within an intravascular system, whereas the circuit 50 and the coaxial cable 51 may have a larger diameter, although the disclosed systems and methods are applicable to a wide variety of impedance matching circuits (e.g., formed from individual discrete components, electronic integrated circuits, other miniaturized circuits).

In receive only mode during RF excitation, RF current may be induced in the antenna 27. In order to resist current induction in the antenna 27 during RF transmission, and obviate resonance of the antenna 27 which may interfere with the flip angle profile, the MR scanner hardware in the RF source 2 of FIG. 1 may provide a positive DC pulse to the antenna 27 for this purpose. The positive DC pulse turns on the PIN diode 56 during RF transmission.

In the exemplary circuit 50, $L_1$ is the distance between PIN diode 56 and the matching capacitor 54, and $L_2$ is the distance between matching capacitor 54 and the point 58 (best shown in FIG. 4) intermediate the poles 33,34 of the loopless antenna 27. The capacitance ($C_2$) of the matching capacitor 54 and the length $L_2$ are chosen such that the input impedance $Z_{IN}$ of the loopless antenna 27 is equal to the characteristic impedance $Z_0$ of the coaxial cable 51. In other words, the length $L_2$ is adjusted in order that when the PIN diode 56 is on, the coaxial cable 29 behaves like an inductor and resonates with the capacitor 54 to disable a current through the loopless antenna 27, although various designs are possible to achieve this desired performance. Then, the length $L_1$ is chosen such that when the PIN diode 56 is turned on, the impedance, $Z_1$, seen by the loopless antenna 27, becomes as large as possible.

In the exemplary embodiment, a substantial portion (i.e., coaxial cable 29) of the length $L_2$ may be inserted within the specimen with the circuit 50 external thereto. The exemplary circuit 50 includes a coaxial cable 60 having a center conductor 62 and outer shield 64. The matching capacitor 54 is electrically interconnected between the center conductor 62 and outer shield 64 at one end of the coaxial cable 60. The DC blocking capacitor 52 is electrically disposed at the other end between the center conductor 62 and the PIN diode 56.

For example, with tap water as the medium, the values of the design parameters are: the capacitance ($C_1$) of the DC blocking capacitor 52 is about 500 pF, $C_2$ is about 70 pF, $L_1$ is about 0.06λ, $L_2$ is about 0.209λ, and $Z_0$ is about 50Ω, with λ being about 2 times the length L of FIG. 4. Regardless of these values, the performance of the circuit 50 is generally not critical since the input impedance $Z_{IN}$ of the loopless antenna 27 is typically of the same order of magnitude as the characteristic impedance of the coaxial cable 51.

An example of an MR scanner usable in the practice of the disclosed systems and methods is the General Electric (G.E.) 1.5 T Signa™ MR scanner, although the disclosed systems and methods are applicable to a wide variety of MR scanners having a wide range of main magnetic field strengths. The MR scanner sources RF pulses to a transmitting coil which transmits such RF pulses in order to excite MR signals. As discussed below in connection with FIG. 7, the loopless antenna 27 may also be employed as an RF pulse transmitting source in addition to employment as a receiver antenna.

Preferably, to obviate insertion of any active or passive electronic components in a blood vessel, a λ/2 cable length, or multiple thereof, is added to the length $L_2$. In this manner, the length of the coaxial cable 29 may be extended by up to about several feet to facilitate MR analysis more deeply within the specimen.

EXAMPLE 3

FIG. 7 is a schematic illustration of the loopless antenna 27, the coaxial cable 29, an impedance matching circuit 66, the coaxial cable 51, and a transceiver 69. The receiver (RX) portion of the transceiver 69, through the switch portion 70 thereof, is employed to receive the responsive output signals from the loopless antenna 27. For matching at the time of manufacture, matching circuit 66 is provided with capacitors 71, 72, which are electrically interconnected to the loopless antenna 27 by the coaxial cable 29. The matching circuit 66 maximizes RF power transfer from the antenna 27 to the RX portion of the transceiver 69 which receives and amplifies the output of the circuit 66. In this embodiment, unlike the embodiment of FIG. 6, there is no PIN diode and the loopless antenna 27 provides a transmitter antenna function as well as a receiver antenna function. The transmitter (TX) portion of the transceiver 69, through the switch portion 70 thereof, is employed to transmit the RF pulses to loopless antenna 27.

The matching circuit 66 is preferably placed nearby the loopless antenna 27, although the length of the coaxial cable 29 may be extended up to about several feet in a similar manner as discussed above in connection with FIG. 6. This is especially advantageous in the case where the loopless antenna 27 and the coaxial cable 29 are employed in the manner of a catheter in vivo. The arrangement of the impedance matching circuit 66 in FIG. 7 is not limiting and it will be understood that other impedance matching, tuning and impedance matching, or impedance matching and decoupling arrangements (e.g., inductor/capacitor, a circuit for shorting the coaxial cable, suitable RF switching circuitry, a coaxial cable having an impedance about equal to the impedance of the loopless antenna) will be evident to those skilled in the art.

EXAMPLE 4

FIG. 8 is a cross-sectional view of a loopless antenna 74 and a coaxial cable 29" positioned in an intravascular system such as, for example, within a blood vessel such as a human vein 76. The vein 76 has an interior bore 78 filled with blood 80, and one or more atherosclerotic plaque deposits, such as plaque deposits 82, which are secured to the interior surface 84 of the vein 76. The antenna 74, in the form shown, is connected to the coaxial cable 29" which, in turn, is connected to a suitable circuit, such as the circuit 50 of FIG. 6 or the circuit 66 of FIG. 7, which serves to match the impedance of the antenna 74 with the impedance of the coaxial cable 51 of FIGS. 6 and 7.

The loopless antenna 74 has a first pole 86 and a second pole 88. The cylindrical outer shield 31 of the coaxial cable 29" is electrically insulated from the center conductor 32 of such cable 29" by the dielectric portion 92 thereof. Unlike the antenna 27 of FIG. 4, the antenna 74 does not have a balancing transformer insulator such as insulator 46.

The second pole 88 includes a cylindrical conductor 94 electrically interconnected with the portion 38 of the inner conductor 32. Preferably, for use in a patient, the end 96 of the cylindrical conductor 94 is suitably rounded to obviate damaging the patient (e.g., the interior surface 84 of the vein 76). In this application, the loopless antenna 74 and coaxial cable 29" are employed in the manner of an invasive probe, such as a catheter, with the matching circuit, such as the circuit 50 of FIG. 6 or the circuit 66 of FIG. 7, located external to the vein 76. The exemplary loopless antenna 74 and coaxial cable 29" are elongated along longitudinal axis 97 with a length of up to about 2 m and an external diameter of about 0.3 mm in order to be received within a blood vessel of a patient.

The antenna 74, cable 29" and suitable matching circuit (not shown) are employable to acquire MR image information or MR chemical shift information about atherosclerotic plaques. For example, as discussed above in connection with FIG. 1, the computer 12 converts the responsive output signals from the antenna 74 into MR image information, and the CRT 16 displays the MR image information in order to image the vein 76. It will be appreciated that the cylindrical conductor 94 may alternatively be employed with the antenna 27 of FIG. 4 for high resolution intravascular and other in vivo applications in a patient. It will further be appreciated that the use of the exemplary antenna 74 and cable 29" may be employed generally simultaneous with a medical, surgical, or interventional procedure on the patient, such as removal of the plaque deposits 82 from the vein 76 by a suitable cutting device (not shown).

Insulating the antenna 74 does not change its electrical properties unless the insulation (not shown) is extensively thick (e.g., greater than about 0.1 mm).

It will be appreciated that the antennas 27 and 74 of FIGS. 4 and 8, respectively, may be employed, for example, in a blood vessel to provide an image and 1-D spectroscopic analysis of plaque built up on the interior of the vessel wall with multislice imaging being provided in an efficient manner due to such elongated antennas being employed. The antennas 27, 74 may also be employed to examine many other characteristics, such as fatty streaks, calcification, sclerosis, and thrombosis, for example. It will further be appreciated that substantially simultaneously with the use of such antennas and coaxial cables 29, 29", medical intervention as, for example, by laser therapy or destruction of the undesired plaque, may be employed. Similarly, any normal diagnostic or therapeutic measures undertaken with the aid of an endoscope (not shown), may be accomplished substantially simultaneously with the use of such antennas for imaging and/or spectroscopic analysis.

EXAMPLE 5

Figure 9:
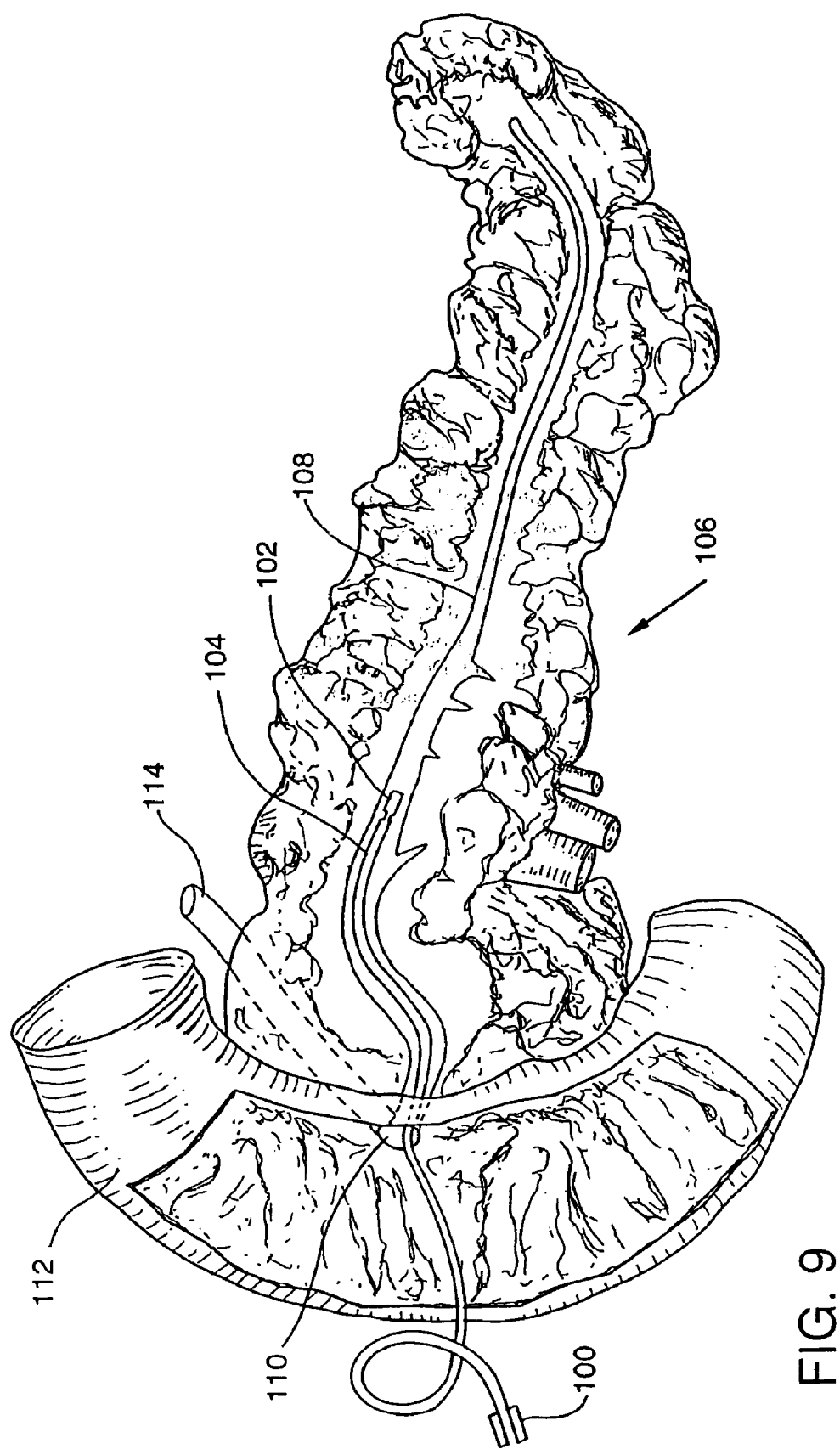
FIG. 9 is a cross-sectional view of a human pancreas with a catheter loopless antenna positioned in the pancreatic duct.

FIG. 9 is a cross-sectional view of a human pancreas 106 with the antenna 102 and a portion of the coaxial cable 104 positioned in a pancreatic duct 108. An external dielectric material 100 may be employed as illustrated with the loopless antenna 102 and coaxial cable 104. The antenna 102 and coaxial cable 104 are employed in the manner of an invasive probe, such as a catheter, during a surgical procedure, associated with the pancreas 106, on the human patient. The antenna 102 and coaxial cable 104 are introduced into the human patient to conduct internal MR analysis thereof.

The antenna 102 and cable 104 have an external diameter which is structured to be received within a naturally occurring passageway in a human being, such as the opening 110 of the pancreatic duct 108. This opening 110, for example, is accessible during surgery on the duodenum 112, although the antenna 102 and cable 104 are structured to be received within a wide variety of naturally open passageways (e.g., bile duct 114, urethra, ureter, esophagus, rectum, ear canal, nasal passage, bronchi, air passages) or man-made passageways in a patient. The antenna 102 and cable 104 are flexible, whereby the same may assume a tortuous path upon insertion into the pancreatic duct 108.

Preferably, the dielectric material 100 is resilient in order to permit flexing of the antenna 102 and cable 104, and return of the same to their original configuration. Any suitable dielectric material having the properties required to function in this environment may be employed. In general, it is preferred that the antenna 102 and cable 104 be covered by about 5 to about 100 microns of such material. A suitable dielectric may, for example, be a bio-compatible plastic material, or blend having the desired properties. The dielectric material employed may, for example, be tetrafluoroethylene, which is sold under the trade designation, "Teflon." It is known for its fine electrical insulating properties, does not interact with any components in water, and can be safely used in blood vessels. The purpose of the dielectric material 100 is to provide bio-compatibility. However, a relatively thick insulation (e.g., greater than about 0.1 mm) will improve SNR at the cost of thickening the antenna 102 and cable 104.

It will be appreciated that the antenna 102, cable 104 and suitable impedance matching circuit are employable with other specimens. For example, the image of the aorta of a live rabbit (not shown) may be obtained. The antenna 102 and cable 104 may be inserted from the femoral artery of the rabbit. Although the rabbit femoral artery is typically very small (e.g., approximately about 1 mm in diameter), catheter-like insertion is easily performed with the exemplary antenna 102 and cable 104.

Any suitable method, such as X-ray fluoroscopic imaging, may be employed to confirm the placement of the antenna 102 in the specimen. It will be appreciated that the placement of the antenna 102 may also be confirmed by a wide variety of other imaging methods. It will further be appreciated that the insertion of the antenna 102 into the patient may be accomplished by direct insertion of the antenna 102 and cable 104 into a suitable blood vessel, by insertion through a catheter guide, and by a wide variety of insertion methods.

Figure 10:
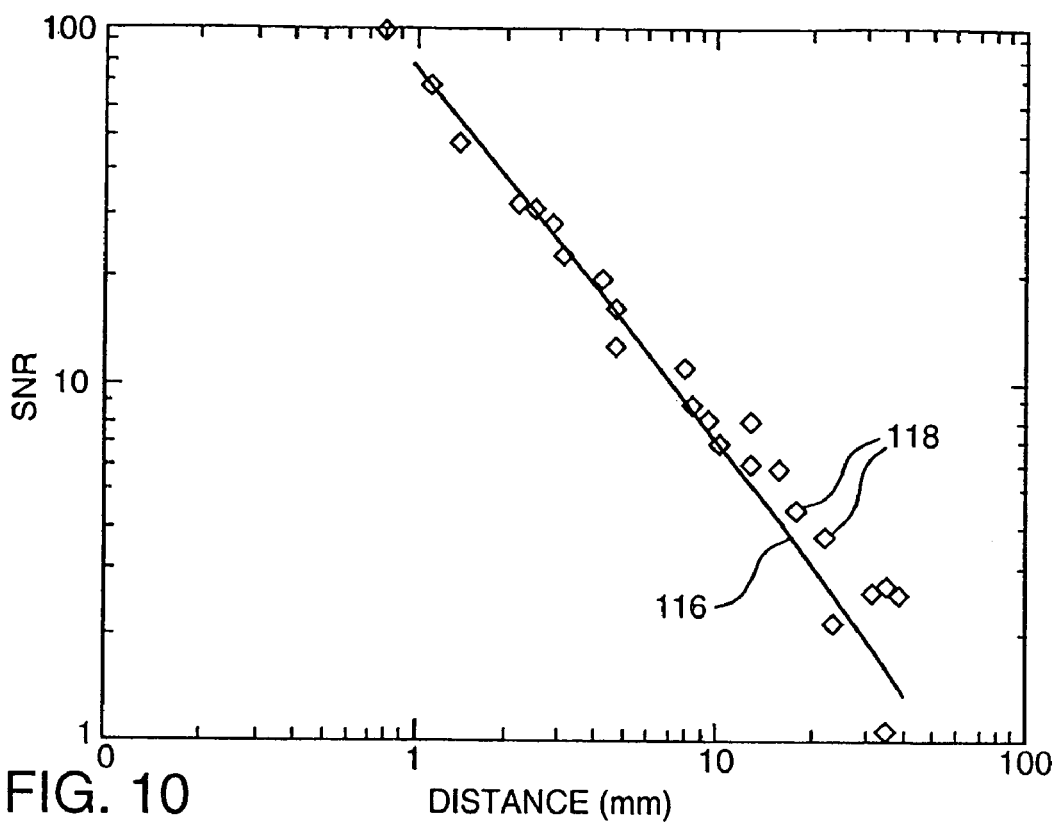
FIG. 10 is a log-log plot of measured and theoretical signal-to-noise ratio with respect to radial distance from the loopless antenna of FIG. 4.

FIG. 10 is a log-log plot of theoretical SNR (shown as a line 116) and measured SNR (shown as discrete diamonds 118) with respect to radial distance from the longitudinal axis 48 of the antenna 27 of FIG. 4. For example, pulse sequences may be employed which allow a voxel size of 0.16×0.16×1.5 mm. Images may be acquired with an 8 cm FOV, 512×512 data acquisition matrix, 1.5 mm slice thickness, 2 NEX, and 16 KHz receiver bandwidth. Such imaging parameters correspond to an effective pixel bandwidth of 0.06 Hz and permit 12 slices of similar images to be obtained in about ten minutes.

The exemplary antenna 27 and cable 29 of FIG. 4, and suitable matching circuit provide a relatively high resolution of the specimen, such as human tissue, to a radial distance of about 10 mm from the longitudinal axis 48, and can be employed to image to radial distances of about 20 mm or greater. Near-microscopic resolution can be obtained in the immediate vicinity of the antenna 27. Increasing the main magnetic field strength improves the resolution significantly and enables imaging with smaller voxel volume.

Figure 11:
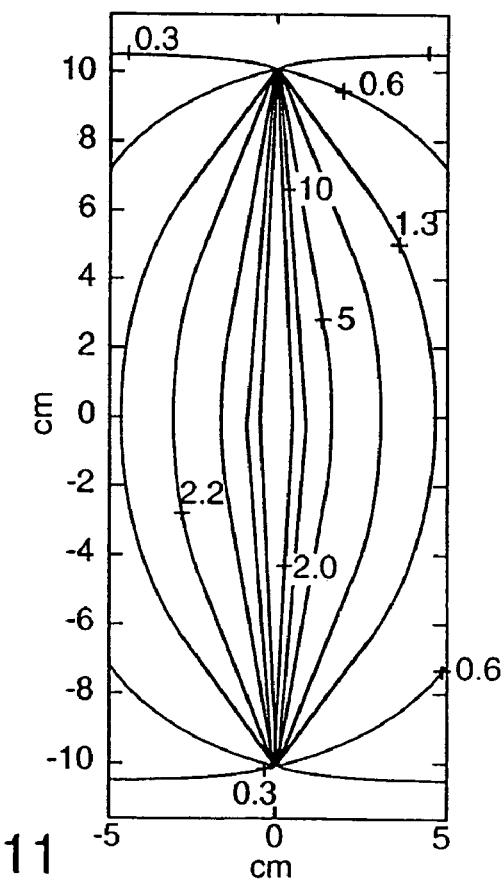
FIG. 11 is a contour plot of theoretical SNR as calculated for a balanced loopless antenna.

FIG. 11 is a contour plot of theoretical SNR as calculated for a balanced loopless antenna similar to the antenna 27 of FIG. 4. The calculation assumes that pulse sequences are employed at 1.5 T main magnetic field strength, with a 160×160×1500 micron voxel size and an effective pixel bandwidth of 0.06 Hz. The units on the horizontal and vertical axes are in centimeters. The balanced loopless antenna is situated in the center of the plot at 0 cm of the horizontal axis and extends from −10 cm to 10 cm of the vertical axis.

EXAMPLE 6

Figure 12:
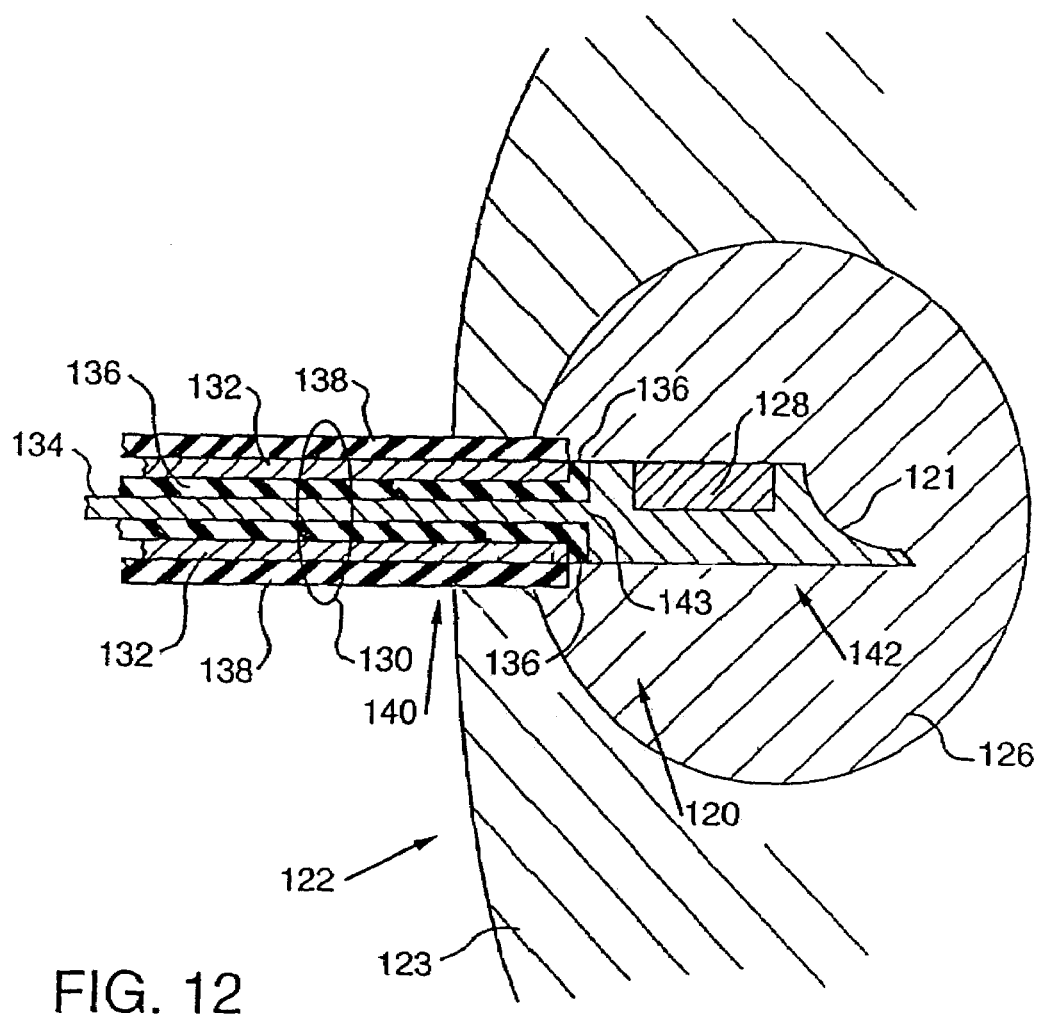
FIG. 12 is a schematic cross-sectional illustration showing a loopless antenna employed as a biopsy needle.

FIG. 12 is a schematic cross-sectional illustration showing a loopless antenna 120 in the form of a biopsy needle 121. The antenna 120 is employed in vivo on a patient 122. The body 123 of the patient 122 contains a lesion 126. The antenna 120 serves to image the lesion 126 in vivo before a sample 128 of the lesion 126 is taken by the biopsy needle 121. This enables more accurate biopsy needle positioning. The antenna 120 is formed at the end of a coaxial cable 130 having an outer shield 132 and an inner conductor 134 which is electrically insulated from such shield 132 by a dielectric portion 136. The biopsy needle 121 can slide inside a non-conducting sheath 138. The antenna 120 has a first pole 140 formed by the shield 132, and a second pole 142 formed by the biopsy needle 121 which is electrically connected to the portion 143 of the inner conductor 134, and which is electrically insulated from the shield 132 by the dielectric portion 136. The antenna 120, coaxial cable 130 and biopsy needle 121 are composed of materials which are magnetic resonance compatible, such as a conductors or dielectric insulators as distinguished from a steel material, for example. The end of the coaxial cable 130 opposite the biopsy needle 121 is preferably electrically interconnected with a suitable impedance matching circuit such as one of the circuits 50 and 66 of FIGS. 6 and 7, respectively.

Figure 13:
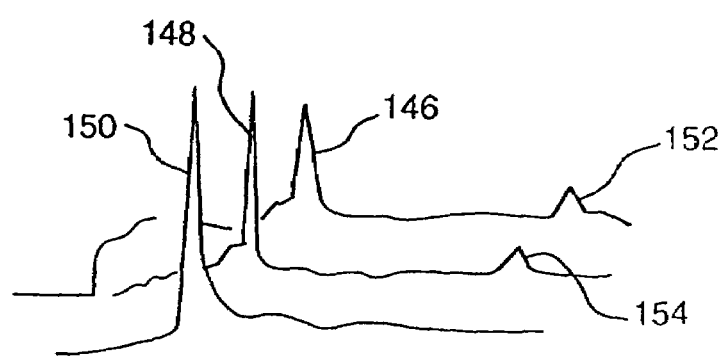
FIG. 13 is a representation of the spectra of three adjacent voxels along the length of the catheter coil of FIG. 2.

FIG. 13 is a representation of the spectra of three adjacent voxels along the length of the catheter coil 18 of FIG. 2 which are established by the computer 12 of FIG. 1 to determine the chemical shift spectra at those locations. It is believed that a comparable spectra may be acquired along the length of the loopless antenna 27 of FIG. 4. The spectra of three adjacent voxels is shown in FIG. 13 with peaks 146,148,150 representing water signals from the three regions and peaks 152,154 from lipid signals in or adjacent to the region of interest, such as blood vessel walls. Water and lipid peaks will tend to vary between normal and atherosclerotic vessels.

EXAMPLE 7

Figure 14:
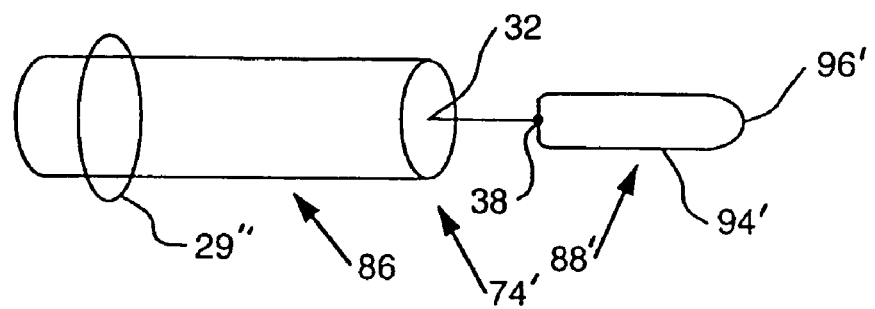
FIG. 14 is a cross-sectional view of another embodiment of a dipole antenna.

FIG. 14 is a cross-sectional view of a coaxial cable 29″ and a dipole antenna 74′ similar to the loopless antenna 74 of FIG. 8. The dipole antenna 74′ has a first pole 86 and a second pole 88′. The second pole 88′ includes a mechanical loop conductor 94′ electrically interconnected with the portion 38 of the inner conductor 32. Preferably, for use in a patient, the end 96′ of the mechanical loop conductor 94′ is suitably rounded to obviate damaging a patient (not shown). The exemplary mechanical loop conductor 94′ has a generally oval shape, although a variety of shapes are considered which are electrically isolated from the first pole 86. This is contrasted with the conventional catheter coil 18 of FIG. 2 in which one of the conductors 19,20 may be connected to a coaxial cable shield and the other conductor may be connected to a coaxial cable inner conductor, thereby forming an electrical loop.

EXAMPLE 8

Figure 15:
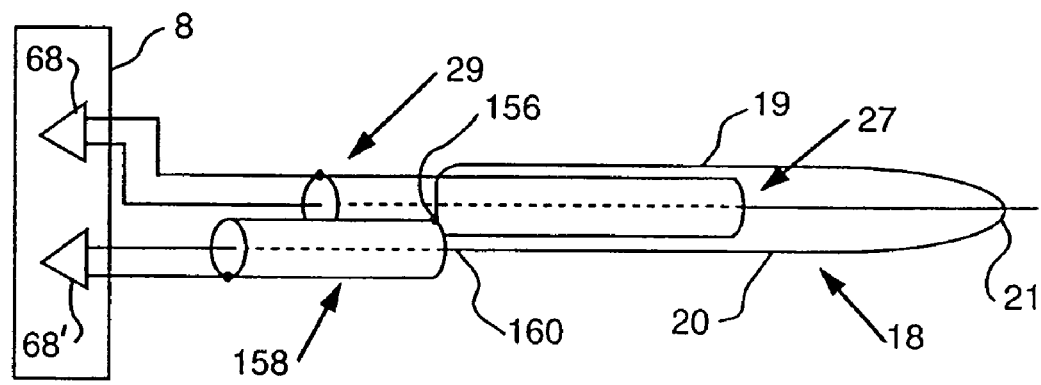
FIG. 15 is a schematic illustration of a loopless antenna employed in combination with a catheter coil.

FIG. 15 is a schematic illustration of the loopless antenna 27 employed in combination with the catheter coil 18 of FIG. 2. The conductor 19 of the catheter coil 18 is connected to outer shield 156 of coaxial cable 158 and the conductor 20 is connected to inner conductor 160 thereby forming an electrical loop. Also referring to FIG. 1, the coaxial cable 158 is connected to one preamplifier 68′ of the receiver 8. The coaxial cable 29 of the loopless antenna 27 is connected to another preamplifier 68 of the receiver 8. Both the coil 18 and the antenna 27 receive MR signals and emit corresponding output signals which are converted by the converter 10 and are received and processed by the computer 12 in order to combine the same into MR information for display by the CRT 16. Preferably, the coil 18 and the antenna 27 are mounted coaxially in order to facilitate use of the better SNR performance of the coil 18 at relatively small distances from the common axis and the better SNR performance of the loopless antenna 27 at relatively large distances therefrom. It will be appreciated that other types and number of coils may be employed with the preamplifier 68′ (e.g., two back-to-back solenoid coils, a pair of quadrature coils) in combination with the antenna 27.

The exemplary antennas 27, 74, 120 disclosed herein increase SNR and provide suitable resolution in MR imaging of blood vessels. The sensitivity of the antennas 27, 74, 120 decays approximately as the inverse of the radial distance from the antenna longitudinal axis. Hence, it provides useful SNR in a cylindrical volume around such antennas. The antennas 27, 74, 120 allow electronic circuits to be placed outside the body and can be easily constructed to a very thin diameter which obviates the size and mechanical property restrictions of catheter coils. The physical dimensions of the antennas 27, 74 make it practical for insertion into blood vessels. The antennas 27, 74, 120 have a low quality factor (Q) and, hence, do not require appreciable tuning when inserted in non-linear intravascular systems.

The simple structure of the antennas 27, 74 makes it possible to construct and operate these devices in a reliable manner in various imaging techniques, such as multislice MRI, 3-D MRI, or 1-D spectroscopy, and in various interventional techniques on a wide variety of specimens. The exemplary loopless antenna 120 and MR compatible biopsy needle 121 facilitate the same in addition to providing the capability of conducting imaging before a biopsy sample is removed from a patient.

Pathogenesis of a blood vessel wall due to atherosclerosis is difficult to characterize by conventional techniques which only investigate the vascular lumen. Intravascular MRI has the unique potential to characterize all three layers of the vessel wall, plaque extent, and composition, as well as thickness and extent of the fibrous cap. The goal of high resolution imaging of atherosclerotic plaques can only be achieved by increasing the SNR of the acquired images. The exemplary antennas 27, 74 greatly increase sensitivity to the target plaque.

The development of new MRI scanners has led to interventional possibilities which will benefit from the intravascular loopless antennas 27, 74. Interventional techniques for atherosclerotic disease may be monitored using real-time, high resolution MR imaging techniques. In addition to precise guidance of laser angioplasty and atherectomy procedures, these apparatus and methods may be used to fully stage lesions and serve as an experimental tool in assessing new therapeutic applications to atherosclerotic disease. Furthermore, with the resulting intravascular MR imaging system, reliable diagnostic information on atherosclerosis may be obtained and MR-guided interventions may be performed with high precision.

It will be appreciated, therefore, that the disclosed systems and methods facilitate enhanced MR imaging and 1-D chemical shift analysis of the interior of a specimen. The loopless antenna 74 provides a generally uniform sensitivity along the longitudinal axis of the dipoles 86, 88 and, as a result of the use of such antenna, facilitates a longer portion of the specimen being imaged with one antenna position. Further, no tuning is required after insertion of the antennas 27, 74, 120 into a specimen. These antennas, in addition to serving solely as a receiver antenna in one embodiment, may in another embodiment function as a transmitter antenna and a receiver antenna. The disclosed systems and methods may be employed generally simultaneously with medical intervention, such as, for example, laser removal of blood vessel plaque.

An embodiment provides enhanced efficiency through the use of at least one of a balancing transformer and an impedance matching circuit.

EXAMPLE 9

Figure 16:
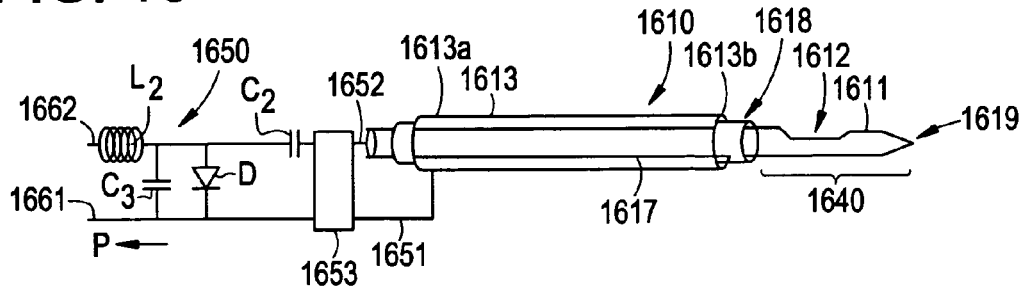
FIG. 16 shows a schematic diagram of a needle antenna and decoupling matching and tuning circuitry.

FIG. 16 shows a schematic diagram of an exemplary embodiment of a needle antenna and associated decoupling matching and tuning circuitry. In the illustrated exemplary embodiment, the needle antenna is a biopsy or sample needle 1610 that permits imaging and sampling of a tissue specimen with a single instrument. A needle according the illustrated exemplary embodiment could be used to obtain a biopsy, or a sample from a variety of structures, including living tissue and inanimate matter. The biopsy needle 1610 and associated circuits 1650 can be fabricated from non-magnetic materials. The biopsy needle 1610 may have a cutting obturator 1611 with side-cut or side-slit 1612. The needle 1610 may have a hollow core near its distal end 1619. The needle can have a cannula or sheath 1613, which can form the shield portion of an MRI antenna, preferably a loopless antenna, and can be electrically connected to the ground or shield side of the decoupling matching and tuning circuit 1650, by connection 1651. An extending portion 1640 of the obturator 1611, may serve as part of the MRI antenna. The obturator 1611, including a portion 1617 thereof can effectively act as an inner conductor of a coaxial cable portion with an outer conductor formed by the cannula 1613. A thin-walled electrically insulating layer 1618, may be located between the obturator 1611 and the cannula 1613. The insulator 1618 may extend at least to as far as the ends 1613a and 1613b of the cannula 1613, to insulate the obturator 1611 in the cannula 1613 up to the side-slit 1612. The insulation layer can be any of a range of known electrical insulators including but not limited to a polymer such as a polyester shrink tubing, fluroethylene polymer, tetrafluoroethylene, polyethylene, silicone, metal oxide, glass, polyethylene terephthalate, or the like. The outside of the cannula 1613 may be covered with an insulating layer, such as with a biocompatible polymer coating.

The biopsy needle 1610 can be connected to decoupling, tuning and matching circuitry 1650 via, e.g., connections 1651 and 1652. These connections can be made directly via one of the many types of detachable RF connector known to those skilled in the art, or, for convenience, via an additional section of thin coaxial cable, which can be permanently attached to circuitry 1650, or attached via a detachable RF connector. The decoupling, tuning and matching circuitry may include a balun 1653, which serves to balance any currents induced on the biopsy needle antenna at the MRI frequency. This can be formed, for example, from an LC tank circuit made by tuning a coil formed by the outer conductor of a coiled piece of coaxial cable, to the MRI resonance frequency with a capacitor, as is known to those skilled in the RF arts. A capacitor, $C_2$, may be provided to block direct current from flowing into the antenna circuit. A (PIN) diode D can be connected across the rails that attach to the loop antenna on the proximal side of $C_2$. A further capacitor, $C_3$, and an inductor, $L_2$, can alone or together be added as tuning and impedance matching elements. The values of $L_2$ and $C_3$, in conjunction with $C_3$, are preferably chosen to tune the antenna formed by the biopsy needle 1610 (cannula 1613 and obturator 1611) to the MRI frequency, and also to substantially match the impedance to the optimum impedance of the MRI scanner receiver input connected at 1661 and 1662. This impedance is preferably that which results in the optimum noise figure of the MRI receiver preamplifier, and is typically 50Ω, the characteristic impedance of standard coaxial cable. Connections 1661 and 1662 can be formed by 50Ω coaxial cable, or connected directly to the MRI receiver input.

Diode D can decouple the antenna during the period when the RF pulses are applied to excite MRI signals. During MRI excitation by an external transmit coil, a DC bias voltage may be provided by the MRI scanner across the coil input, causing the diode to conduct. During conduction, the tuning elements can be shorted-out, which results in detuning of the loopless antenna biopsy needle, and high impedance, thereby limiting those RF currents induced at the MRI frequency in the loop.

Figure 17:
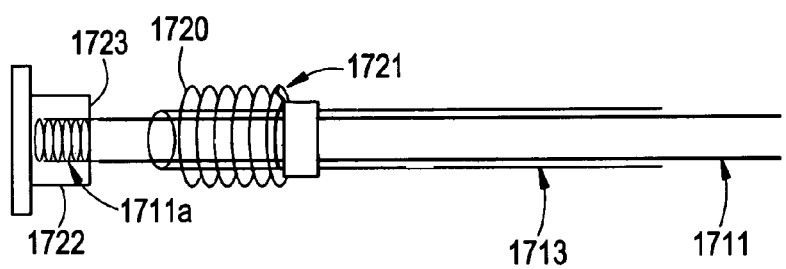
FIG. 17 shows a schematic diagram of the electrical connections to the proximal end of the biopsy-needle-antenna.

FIG. 17 illustrates exemplary electrical connections of the exemplary biopsy needle MRI antenna described above in connection with FIG. 16, and a plunger mechanism for activating the acquisition of a biopsy specimen, in accordance with an embodiment. The cannula 1713, which can function as the shield, may be electrically connected to a loading spring 1720 by a joint 1721. The spring 1720 may be non-magnetic. Joint 1721 may be a wire. The spring 1720 can thereby serve two purposes. First, the spring 1720 may act as a compression spring to load and trigger the movement of the cannula 1713 that cuts the tissue. Second, the spring 1720 can act as a deformable conductor that connects the shield that can be formed at least in part by the cannula 1713, to the matching circuitry 1650 at connector 1651 in FIG. 16. The electrical connection can be made, e.g., by connecting the spring 1720 to lead 1651, which in an embodiment is the outer shield of a section of flexible coaxial cable.

The proximal end 1711*a* of the obturator 1711 can be secured to, e.g., a plunger button 1722. The proximal end 1711*a* may be covered with, e.g., ultraviolet cure adhesive. An electrical connection 1723 can be made from the proximal end 1711*a* of the obturator 1711, which can form the inner conductor of an MRI antenna, to the connection 1652 of the tuning matching and decoupling circuit 1650, as depicted in FIG. 16. In an embodiment, the device may include a flexible coaxial cable connection (not shown) between the needle antenna and circuitry 1650. Connection 1652 may preferably be the inner conductor of the coaxial cable.

Figure 18:
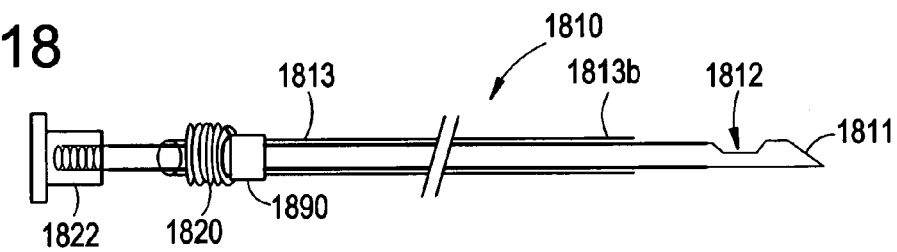
FIGS. 18 and 19 depict two exemplary positions that a biopsy needle can adopt.
Figure 19:
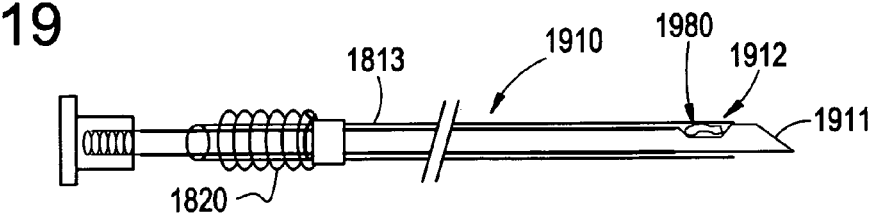

FIGS. 18 and 19 depict two exemplary positions that a biopsy needle can adopt. FIG. 18 shows a biopsy needle 1810 in a charged position. In this position, the spring 1820 is compressed. The obturator 1811 can be rigidly coupled to the plunger 1822 and slideably displaceable relative to the cannula 1813. As the plunger 1822 is pulled in a proximal direction, a plastic clip 1890 can compress the spring 1820. The side-slit 1812 of the obturator 1811 can be exposed, and the cannula 1813 can be retracted relative to the obturator 1811. FIG. 19 depicts a biopsy needle 1910 in an uncharged position. The spring 1920 can be relaxed. The side-slit 1912 of the obturator 1911 can be covered by the cannula 1913. A biopsy 1980 can be coupled to the biopsy needle antenna 1910. In this exemplary embodiment, the biopsy 1980 is trapped between the cannula 1913 and the obturator 1911, in the side-slit 1912.

With reference to FIG. 18, to operate the tissue sampling function of the biopsy needle 1810, the plunger 1822 can be pulled in the proximal direction, which can charge the loading spring 1820 until a locking mechanism (not shown) locks in place. The locking mechanism may include, e.g., a notch. Once the spring is locked, the plunger 1822 may be freely pushed or pulled, thereby advancing or retracting the obturator 1811 out from or into the cannula 1813, respectively. A high quality image may be obtained in a variety of obturator positions, particularly when the obturator 1811 is extended from the cannula 1813, as depicted. Once the needle has been positioned for the biopsy or sampling, the plunger 1822 may be forcefully pushed distally. This can release the locking mechanism so that the cannula 1813 is propelled forward by the releasing spring 1820. A sharp-edged front-end 1813*b* of the cannula cuts the tissue sample intact within the slide-slit portion 1812 as the biopsy needle transitions to the state depicted in FIG. 19.

Figure 20:
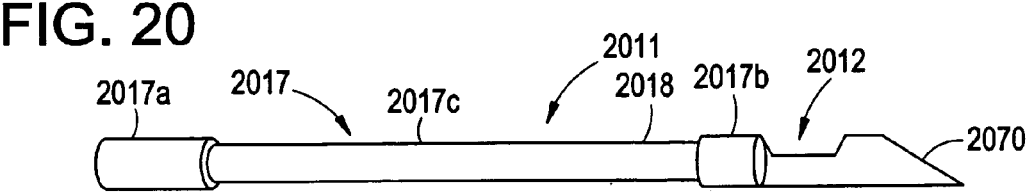
FIG. 20 shows a diagram of an obturator of a biopsy needle antenna.

FIG. 20 illustrates an exemplary embodiment of an obturator 2011 in more detail. The obturator 2011 can have a distal end 2070. The distal end 2070 can be sharp and designed for piercing, e.g., tissue. The obturator 2011 can have a side-slit 2012 for receiving a portion of a tissue as a biopsy (not shown). The obturator 2011 can have a shaft 2017. The shaft can serve as the inner conductor of a coaxial cable. The obturator 2011 can be covered by an insulator 2018. The insulation may include, for example, a shrink-tubing that can fit snugly over the obturator 2011. The insulator can fill the space between the obturator 2011 and a cannula (not shown). The insulator 2018 can fill a portion of the space between the obturator 2011 and the cannula. Air can fill at least a portion of the space between the obturator 2011 and the cannula. The insulator may include a lubricious substance to facilitate sliding of the cannula over the obturator 2011, or sliding of the obturator 2011 within the cannula. A lubricious coating (not shown) may cover the insulator 2018 for similar purposes. The insulator 2018 and lubricious substance or coating may include suitable materials described herein. In an embodiment, the obturator 2011 has a diameter of 0.067" at distal region 2017*b* and proximal region 2017*a*, and a reduced diameter of 0.055" in region 2017*c* to accommodate an insulation layer of 0.010" thickness. In an embodiment, the movement of the obturator 2011 inside the cannula 2013 is not obstructed. The thin section can be covered with electrical insulation 2018, as detailed above. Insulation 2018 can function as both electrical insulation and dielectric portion of the antenna. The specific dimensions described are provided for illustrative purposes and are not intended to be limiting. It will be understood to one skilled in the art that such needle biopsy antenna devices can be fabricated for a variety or range of different sizes, for example, with an obturator diameter in the range of 0.03" to 0.15".

Figure 21:
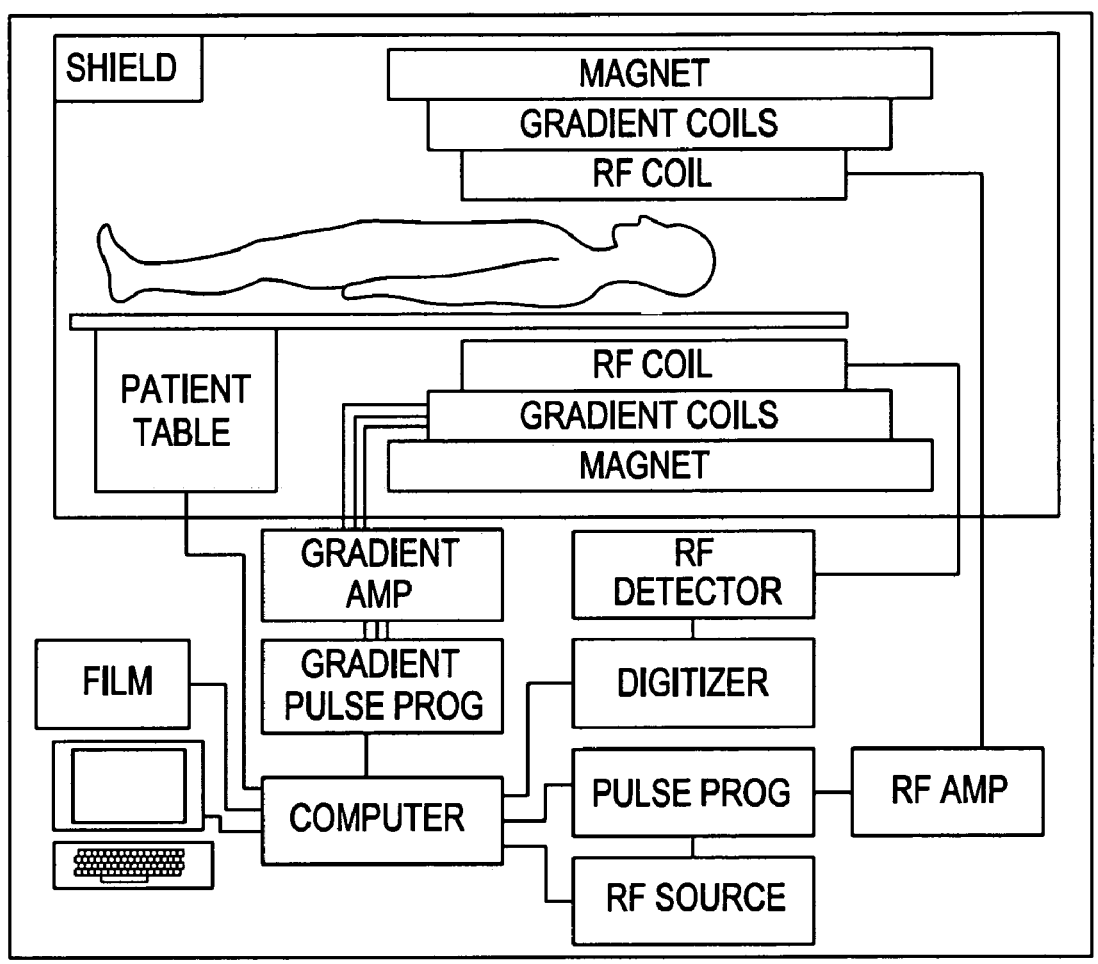
FIG. 21 shows a block diagram illustrating the operation of an MRI scanner system.

FIG. 21 shows a block diagram illustrating the operation of an MRI scanner system, which may be used in connection with an embodiment. A magnet can provided for creating the magnetic field necessary for inducing magnetic resonance. Within the magnet can be X, Y, and Z gradient coils for producing a gradient in the static magnetic field in three orthogonal directions. Within the gradient coils may be an external RF excitation coil. The external RF excitation coil can produce the magnetic field necessary to excite the MRI signals in the body. A computer can be provided for controlling all components in the MRI scanner. This includes the RF frequency source, spectrometer and pulse programmer. The pulse programmer can generate a controlled time-sequence of shaped and/or phase or frequency-modulated RF pulses that are delivered to the RF power amplifier. The RF power amplifier may have pulse power of 1–20 kW, which is applied to the external RF excitation coil. The computer can also control the gradient magnetic field by providing a sequence of modulated pulses that are synchronous with the RF pulse sequence, to gradient power amplifiers, which in turn activate the X, Y, and Z gradient magnetic field coils in the magnet. Signals detected by receiver coils in response to the applied RF/gradient imaging sequences, including those detected in the aforementioned multi-functional MRI catheter system, can be coupled to a receiver preamplifier. These signals may be amplified, phase sensitive detected, for example, by converting to digital signals and being fed to a digital receiver. The digital image data may then be reconstructed in the computer and displayed as images on a monitor or the like.

An embodiment provides accurate localization of the biopsy needle tip. Because the needle antenna is a receiver it can be used to directly image the tissue around it. This image can be viewed on with high resolution employing the needle antenna receiver disclosed herein, or, it can be viewed at low resolution as an overlay on a large field-of-view "scout" image obtained with an auxiliary coil outside the body. The location of the needle antenna can be tracked in the body, by the bright line of signal moving in the scout image. The scout image can be updated at an interval set by the user to compensate for patient motion. An interactive control can allow the physician to "zoom in" towards the bright catheter, finally resulting in a high-resolution image in the area of the distal needle tip. The "zoom" function can be achieved with interactive control of the imaging gradients.

EXAMPLE 10

Figure 22A:
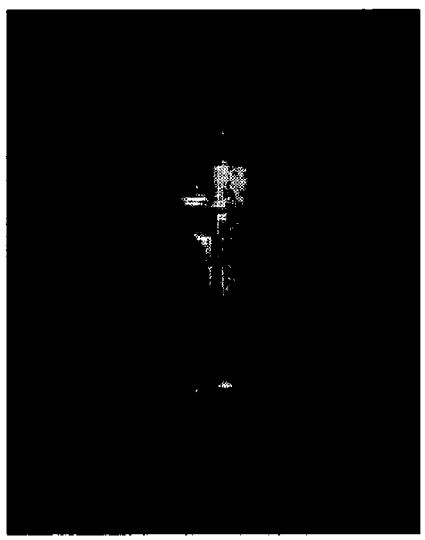
FIGS. 22A and 22B show images acquired with a biopsy needle antenna.
Figure 22B:
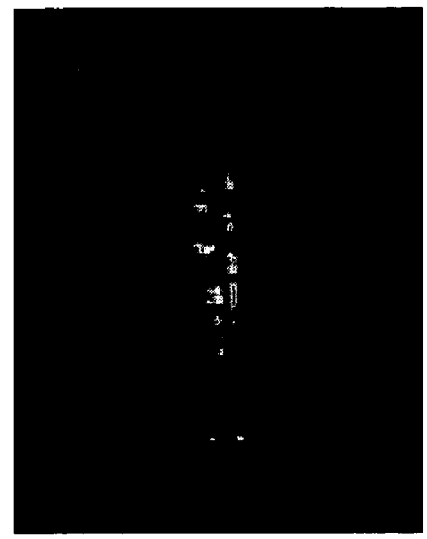

FIGS. 22A and 22B show images acquired with an MRI biopsy needle. FIG. 22A depicts a bovine kidney with a biopsy needle antenna inserted therein. The uniform signal intensity of the kidney is typical of renal MRI imaging. The needle antenna is clearly discernable. FIG. 22B depicts a lemon with a biopsy needle antenna inserted therein. The radiating fibrous structure is readily visible, as are seeds inside the lemon. The biopsy needle position is accurately localized with respect to the lemon.

Figure 23A:
FIGS. 23A–F depict a sequence of images from an image-guided biopsy procedure.
Figure 23B:
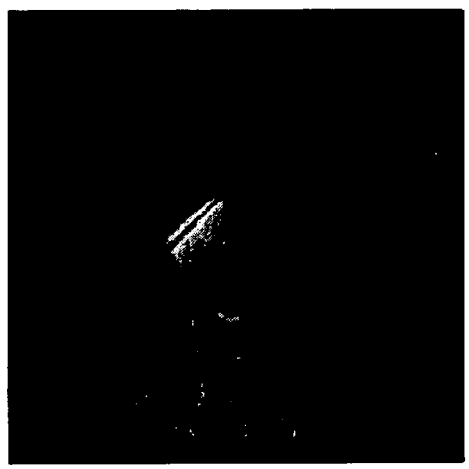
Figure 23C:
Figure 23D:
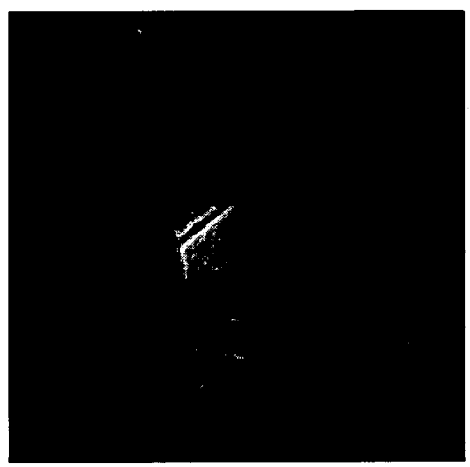
Figure 23E:
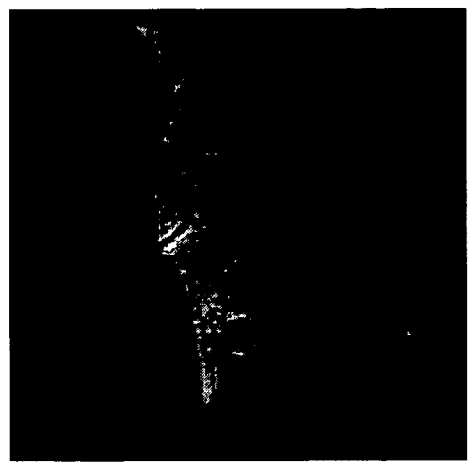
Figure 23F:

FIGS. 23A–F depict a sequence of images from an image-guided biopsy procedure. FIG. 23A depicts the initial introduction of a biopsy needle antenna into the pig anatomy. FIG. 23B depicts deeper insertion. FIG. 23C depicts full insertion of the biopsy needle antenna prior to biopsy acquisition. FIG. 23D depicts the biopsy needle antenna after biopsy acquisition. FIG. 23E depicts withdrawal of the biopsy needle antenna. FIG. 23F depicts the pig anatomy after the biopsy needle has been withdrawn completely.

Preferred embodiments may include an MRI biopsy needle; an MRI biopsy needle connected and used in conjunction with matching tuning decoupling circuitry; an MRI biopsy needle and matching tuning decoupling circuitry used in conjunction with an MRI scanner; and a method for performing image-guided biopsies employing an MRI biopsy needle antenna, tuning matching and decoupling circuitry in conjunction with an MRI scanner.

While for clarity of disclosure reference has been made herein to display means for displaying an image, it will be appreciated that the image information may be stored, printed on hard copy, be computer modified, or be combined with other data. All such processing shall be deemed to fall within the terms "display" or "displaying" as employed herein.

Various alternative embodiments are envisioned within the scope of the disclosed systems and methods. Figures provide illustration of some inventive aspects of the disclosed systems and methods. Therefore, relative or absolute dimensions in the Figures should be understood as exemplary and not as limiting. Whereas particular embodiments have been described herein for purposes of illustration, it will be appreciated by those skilled in the art that numerous variations of the details may be made without departing from the disclosed systems and methods as described in the following claims.

We claim:

1. A biopsy needle antenna, comprising:
   a magnetic resonance imaging antenna, having:
   an outer shield; and
   an inner conductor electrically insulated from the outer shield by a dielectric; and
   a biopsy needle electrically connected to the inner conductor and electrically insulated from the outer shield by the dielectric.

2. The biopsy needle antenna of claim 1, further comprising a sheath, the biopsy needle being slideably displaceable within the sheath.

3. The biopsy needle antenna of claim 2, wherein the sheath is defined by the outer shield.

4. The biopsy needle antenna of claim 1, wherein at least one of the outer shield, the inner conductor, and the biopsy needle comprise a magnetic resonance compatible material.

5. The biopsy needle antenna of claim 1, wherein the biopsy needle antenna is configured with circuitry that receives magnetic resonance spectroscopy information from a sample.

6. The biopsy needle antenna of claim 1, wherein the outer shield and the inner conductor form a coaxial cable.

7. The biopsy needle antenna of claim 6, wherein the coaxial cable is electrically interconnected to an impedance matching circuit.

8. The biopsy needle antenna of claim 1, wherein at least one of the outer shield, the inner conductor, and the biopsy needle comprise a superelastic material.

9. The biopsy needle antenna of claim 1, wherein the outer shield is slideably displaceable with respect to the inner conductor.

10. The biopsy needle antenna of claim 1, wherein the inner conductor comprises an obturator and the outer shield comprises a cannula slideably displaceable over the obturator.

11. The biopsy needle antenna of claim 10, wherein the obturator further comprises a side-slit.

12. The biopsy needle antenna of claim 11, wherein the cannula comprises a distal end having a cutting edge, the cutting edge slideably displaceable over the side-slit.

13. The biopsy needle antenna of claim 11, wherein the cannula covers at least the side-slit.

14. The biopsy needle antenna of claim 10, wherein the cannula is spring-loaded.

15. The biopsy needle antenna of claim 10, wherein at least a portion of the obturator protrudes from a distal end of the cannula.

16. The biopsy needle antenna of claim 1, further comprising a spring coupled to the outer shield.

17. The biopsy needle of claim 16, wherein the spring is electrically coupled to the outer shield.

18. The biopsy needle antenna of claim 1, wherein the dielectric comprises at least one of fluroethylene polymer, tetrafluoroethylene, polyester, polyethylene, silicone, metal oxide, glass, and polyethylene terephthalate.

19. The biopsy needle antenna of claim 1, wherein the dielectric is covered by a lubricious coating.

20. The biopsy needle antenna of claim 19, wherein the lubricious coating comprises at least one of polyvinylpyrrolidone, polyacrylic acid, and silicone.

21. The biopsy needle antenna of claim 1, wherein the inner conductor and outer shield are electrically coupled to an interface.

22. The biopsy needle antenna of claim 21, wherein the interface comprises at least one of a tuning-matching circuit, a balun circuit, a decoupling circuit, and a variable capacitor.

23. The biopsy needle antenna of claim 21, wherein the interface resides upstream of the biopsy needle and is configured to couple to an MRI scanner.

24. A sampling needle antenna, comprising:
   a cannula being formed at least in part of a conductive material and defining an outer shield;
   an obturator being formed at least in part of a conductive material and defining an inner conductor, the obturator being slideably displaceable relative to the cannula; and
   an insulator electrically insulating the cannula from the obturator;
   wherein the outer shield, the inner conductor, and the insulator form a magnetic resonance imaging antenna.

25. A method of obtaining a sample with magnetic resonance imaging guidance, comprising:
   providing a magnetic resonance imaging antenna, wherein the magnetic resonance imaging antenna comprises an outer shield and an inner conductor electrically insulated from the outer shield by a dielectric, and wherein a sampling needle is electrically connected to the inner conductor and electrically insulated from the outer shield by the dielectric;

advancing the antenna to a structure from which the sample is to be taken;

detecting magnetic resonance data by the antenna; and coupling the sample to the antenna and the sampling needle whereby the sample is obtained.

26. The method of claim 25, wherein the sample is a biopsy.

27. The method of claim 25, wherein the inner conductor comprises anobturator and the outer shield comprises a cannula, the obturator slideably displaceable relative to the cannula.

28. The method of claim 25, further comprising coupling the magnetic resonance data to an MRI scanner to form a magnetic resonance image.

29. The method of claim 28, wherein the image formed is a composite image.

30. The method of claim 28, wherein the image formed is a high resolution image.

31. A method of obtaining a sample with magnetic resonance imaging guidance, comprising:

providing a sampling needle magnetic resonance imaging antenna;

advancing the antenna to a structure from which the sample is to be taken;

detecting magnetic resonance data by the antenna; and coupling the sample to the antenna, wherein the antenna comprises a cannula including an outer shield, an obturator including an inner conductor, the obturator slideably displaceable relative to the cannula, and an insulator electrically insulating the outer shield from the inner conductor; and wherein the coupling includes trapping the sample between the cannula and the obturator.

32. The method of claim 31, wherein trapping includes moving at least one of the cannula and the obturator relative to the other.

33. A method of obtaining a magnetic resonance imaging-guided biopsy, comprising:

providing a biopsy needle antenna, having:

a magnetic resonance imaging antenna, including:

an outer shield; and an inner conductor electrically insulated from the outer shield by a dielectric; and a biopsy needle electrically connected to the inner conductor and electrically insulated from the outer shield by the dielectric;

advancing the needle to a lesion;

imaging the lesion with the antenna; and taking a sample of the lesion with the needle.

* * * * *

UNITED STATES PATENT AND TRADEMARK OFFICE
CERTIFICATE OF CORRECTION

| | | |
|---|---|---|
| PATENT NO. | : 7,236,816 B2 | Page 1 of 1 |
| APPLICATION NO. | : 10/131601 | |
| DATED | : June 26, 2007 | |
| INVENTOR(S) | : Kumar et al. | |

It is certified that error appears in the above-identified patent and that said Letters Patent is hereby corrected as shown below:

<u>In The Claims:</u>

Column 29, Claim 27, Line 9:  Please correct "anobturator"
                                      To read -- an obturator--

Signed and Sealed this

Second Day of October, 2007

JON W. DUDAS
*Director of the United States Patent and Trademark Office*